US010710068B2

(12) United States Patent
Brown et al.

(10) Patent No.: US 10,710,068 B2
(45) Date of Patent: Jul. 14, 2020

(54) MICROFLUIDIC CHIP WITH CHEMICAL SENSOR HAVING BACK-SIDE CONTACTS

(71) Applicant: e-SENS, Inc., Salt Lake City, UT (US)

(72) Inventors: Richard B. Brown, Salt Lake City, UT (US); Ondrej Novak, North Salt Lake, UT (US)

(73) Assignee: e-SENSE, Inc., Salt Lake City, UT (US)

( * ) Notice: Subject to any disclaimer, the term of this patent is extended or adjusted under 35 U.S.C. 154(b) by 220 days.

(21) Appl. No.: 15/710,823

(22) Filed: Sep. 20, 2017

(65) Prior Publication Data
US 2019/0083980 A1    Mar. 21, 2019

(51) Int. Cl.
| | |
|---|---|
| *G01N 33/487* | (2006.01) |
| *B81B 7/02* | (2006.01) |
| *B01L 3/00* | (2006.01) |
| *G01N 27/00* | (2006.01) |

(52) U.S. Cl.
CPC ... *B01L 3/502715* (2013.01); *B01L 3/502707* (2013.01); *G01N 33/48707* (2013.01); *B01L 2200/12* (2013.01); *B01L 2300/0627* (2013.01); *B01L 2300/0645* (2013.01); *B01L 2300/0816* (2013.01); *B01L 2300/0887* (2013.01); *B01L 2400/086* (2013.01); *G01N 27/00* (2013.01)

(58) Field of Classification Search
None
See application file for complete search history.

(56) References Cited

U.S. PATENT DOCUMENTS

| | | | |
|---|---|---|---|
| 5,700,360 A | 12/1997 | Chan et al. | |
| 5,900,128 A | 5/1999 | Gumbrecht et al. | |
| 6,072,322 A * | 6/2000 | Viswanath | G01R 1/0483 |
| | | | 324/750.05 |
| 6,764,652 B2 | 7/2004 | Hower et al. | |
| 7,258,837 B2 | 8/2007 | Yager et al. | |
| 7,438,851 B2 | 10/2008 | Hower et al. | |
| 7,988,838 B2 | 8/2011 | Dipiazza et al. | |
| 9,017,611 B2 | 4/2015 | Lin et al. | |
| 9,670,445 B1 | 6/2017 | Kuo et al. | |

(Continued)

FOREIGN PATENT DOCUMENTS

| | | |
|---|---|---|
| EP | 1353751 | 4/2011 |
| WO | WO 2002/058846 | 8/2002 |

OTHER PUBLICATIONS

Franklin, Robert K. et al., "2.12 Chemical Sensors", The University of Michigan Ann Arbor, MI, Sensicore, Inc., Ann Arbor, MI, The University of Utah, Salt Lake City, UT, Elsevier B.V., 2008 (pp. 432-461) (29 pages).

(Continued)

*Primary Examiner* — Paul S Hyun
(74) *Attorney, Agent, or Firm* — Alliance IP, LLC

(57) ABSTRACT

Aspects of the embodiments are directed to a microfluidic chip and methods of making the same. The microfluidic chip can include a sensor device residing on the microfluidic chip, the sensor-side comprising a chemical sensor and the backside including a backside electrode, the chemical sensor electrically coupled to the backside electrode by a via; a microfluidics channel in the microfluidic chip, the sensor-side of the sensor device facing the microfluidics channel; and a metal contact electrically connected to the backside electrode.

16 Claims, 28 Drawing Sheets

(56) References Cited

U.S. PATENT DOCUMENTS

2006/0141469 A1    6/2006  Rossier et al.
2008/0308418 A1   12/2008  Dipiazza et al.
2010/0155239 A1    6/2010  Sørensen et al.
2010/0165784 A1*  7/2010  Jovanovich ......... B01F 11/0045
                                                          366/163.2

OTHER PUBLICATIONS

PCT International Search Report and Written Opinion in PCT International Application Serial No. PCT/US2018/051825 dated Jan. 23, 2019 (12 pages).
EPO Extended European Search Report in EP Application Serial No. 17824978.5 dated Jan. 27, 2020 (10 pages).

* cited by examiner

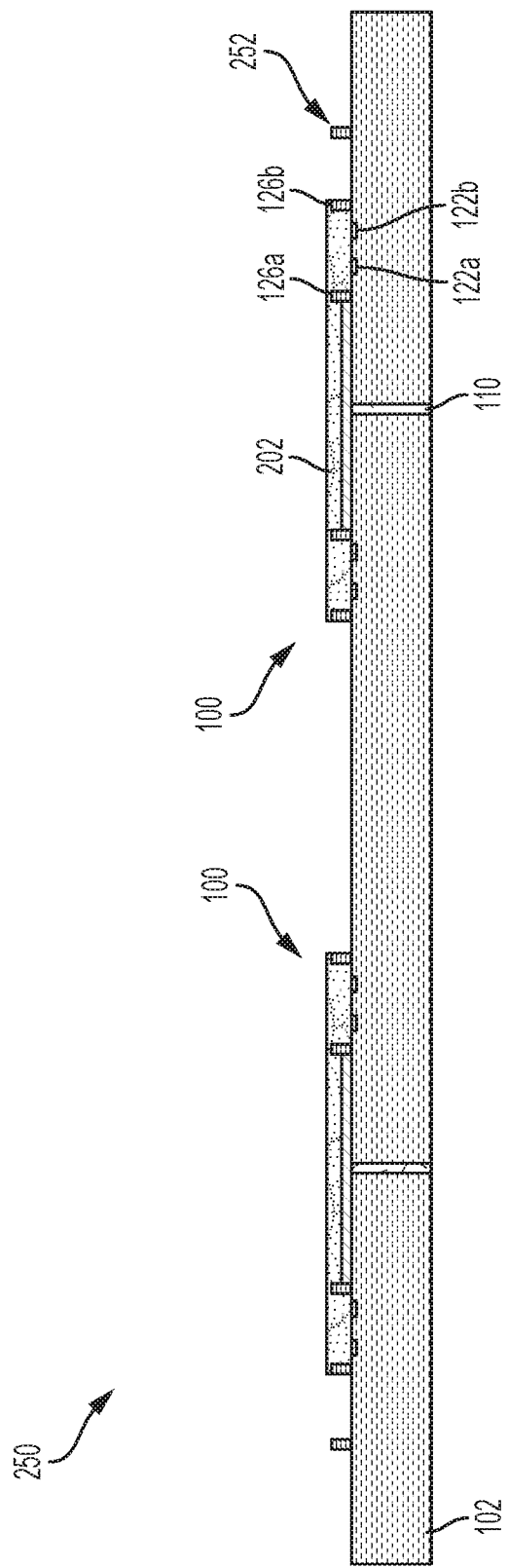

A-A

B-B

B-B(ALT)

B-B(ALT)

B-B (ALT)

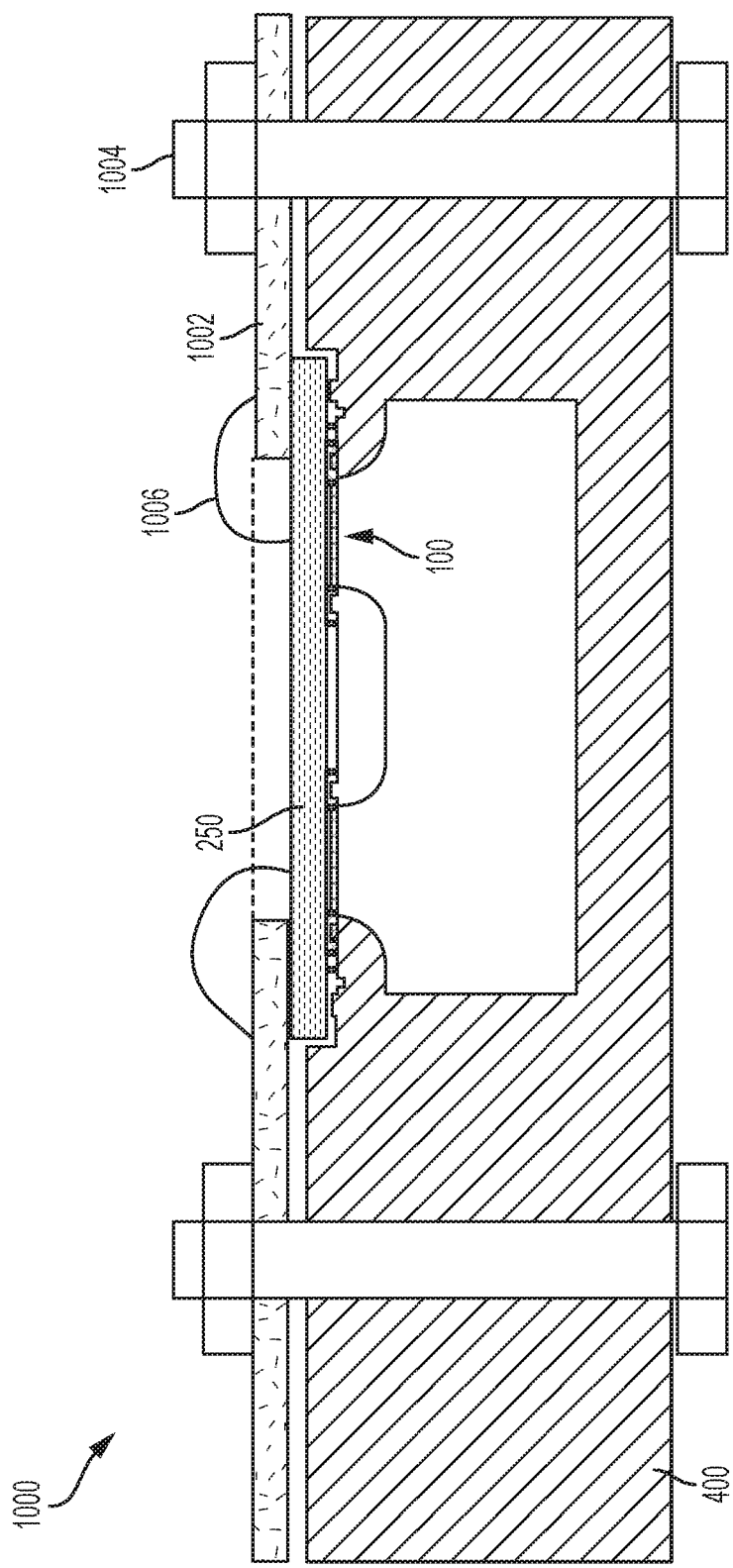

MICROFLUIDIC CHIP WITH CHEMICAL SENSOR HAVING BACK-SIDE CONTACTS

TECHNICAL FIELD

This disclosure pertains to microfluidics chips, and more particularly, to microfluidic chips with chemical sensor dies having back-side contacts for making electrical contact to the sensors.

BACKGROUND

Chemical sensors can be fabricated using semiconductor technology. The use of semiconductor manufacturing can result in a reduction of size of the chemical sensor as well as mass fabrication of chemical sensors, thereby reducing per unit cost of each sensor. More generally, the use of semiconductor manufacturing to manufacture sensors produces the same or similar benefits as it does for electrical circuits: low cost per sensor, small size, and highly reproducible behavior.

Semiconductor manufacturing technology provides precise control of layer thickness and lateral dimensions, so that the sensors can be miniaturized, and so that they will have well-controlled characteristics. By making the sensors small, sample volumes can be small (which may not be important in testing water, but may be important in testing other solutions, such as blood samples from newborns). But operation of the sensors also requires rinsing between samples, storage in a controlled solution, and calibration with reference solutions. Volumes of all of these solutions can be smaller if the sensors are miniaturized, as they are on the silicon substrates.

SUMMARY

Aspects of the embodiments are directed to a microfluidic chip that includes a sensor device residing on the microfluidic chip, the sensor device including a substrate including a sensor-side and a backside, the sensor-side comprising a chemical sensor and the backside including a backside electrode, the chemical sensor electrically coupled to the backside electrode by a via; a microfluidics channel in the microfluidic chip, the sensor-side of the sensor device facing the microfluidics channel; and a metal contact electrically connected to the backside electrode.

Aspects of the embodiments are directed to a method for forming a microfluidic system including a sensor device, the method including providing a microfluidic chip, the microfluidic chip including a sensor device mounting surface, the sensor device mounting surface including a negative space revealing a microfluidic channel and a ledge residing over the microfluidic channel; providing an adhesive on the ledge; providing a sensor device on the ledge and securing the sensor device on the ledge by the adhesive, the sensor device including a sensor side and a backside, the sensor device positioned on the ledge with the sensor side facing the microfluidic channel; electrically connecting a backside electrode on the sensor device to a secondary electrode; and providing an encapsulant on the sensor device, the electrical contact on the printed circuit board, and the wire bond.

In some embodiments, the sensor-device includes one of an ion-selective sensor, an amperometric sensor, a thermal sensor, a conductivity sensor, a temperature sensor, or an oxidation reduction potential (ORP) sensor.

In some embodiments, the sensor device may include a through silicon via electrically connecting the backside electrode to a sensor-side electrode on the sensor-side.

Embodiments may also include an encapsulant covering the sensor device backside and the metal contact.

Embodiments may also include a reference electrode downstream in the microfluidics channel from the sensor die.

Embodiments may also include a sensor die, the sensor die including a plurality of sensor devices.

In some embodiments, the microfluidic chip includes a cutout portion, the cutout portion including a ledge, and wherein the sensor device is rigidly affixed to the ledge of the cutout.

Embodiments may also include a printed circuit board (PCB), the PCB including an electrical contact, the metal contact including a wire electrically connected to the PCB electrical contact and electrically connecting the PCB electrical contact to the backside electrode.

In some embodiments, the metal contact includes one or more of a POGO pin electrical interface, gold bumps, pressure contacts, or wire bonds.

In some embodiments, the sensor device is a first sensor device, and the microfluidic chip further includes a second sensor device downstream of the first sensor device.

In some embodiments, the first sensor device includes one of a potentiometric sensor or an amperometric sensor and the second sensor device includes one of an amperometric sensor or a potentiometric sensor, respectively.

In some embodiments, the microfluidic chip includes a clamping structure, the clamping structure including at least one raised portion to engage with a membrane of the sensor device to secure the sensor device to the microfluidic chip.

In some embodiments, the microfluidic channel includes a serpentine shaped channel disposed below the sensor device.

Embodiments may also include providing a printed circuit board onto the microfluidic chip, the printed circuit board including an electrical contact pad; wherein electrically connecting the backside electrode on the sensor device to the secondary electrode includes wire bonding the backside electrode to the electrical contact pad.

In some embodiments, the backside electrode is electrically coupled to a sensor on the sensor side of the sensor device.

In some embodiments, the sensor side includes one of a chemical sensor, an amperometric sensor, a thermal sensor, a conductivity sensor, a temperature sensor, or an oxidation reduction potential (ORP) sensor.

BRIEF DESCRIPTION OF THE DRAWINGS

FIG. 2B is a schematic diagram of a sensor die that includes multiple sensor devices in accordance with embodiments of the present disclosure.

FIG. 10A is a schematic diagram of a side sectional view of a sensor die clamped to a microfluidic chip and secured to the microfluidic chip by screws in accordance with embodiments of the present disclosure.

Figures are not drawn to scale.

DETAILED DESCRIPTION

This disclosure describes a microfluidic chip that includes a microfluidic channel that traverses one or more sensor receiving areas. The one or more sensor receiving areas can include an ion selective sensor, an amperometric sensor, thermal sensor, conductivity sensor, temperature sensor, and/or oxidation reduction potential (ORP) sensor, or other sensors.

The microfluidic chip of the present disclosure facilitates electrical connections to be made to the sensor backsides, as opposed to using electrical connections on the front side of the chip. Front side connections can be facilitated by wire bonds, C4 bumps, conductive polymer in zebra strips, pogo pins, etc. Any of these techniques make it impractical to mount the sensors over a microfluidic channel because these types of connections can protrude above the sensors. If the connections are in the channel, the connections also have to be insulated from the solution, thereby increasing channel size and making the channel difficult to rinse.

As mentioned above, microfluidic chemical analysis can include different types of sensors, such as ion selective sensors, amperometric sensors, thermal sensors, conductivity sensors, temperature sensors, and/or oxidation reduction potential (ORP) sensors, or other sensors. Each of these aforementioned chemical sensors can include a through-silicon via, facilitating placing electrical contacts on the backside of the sensor.

An example chemical sensor is described in U.S. patent application Ser. No. 15/204,371 filed on Jul. 7, 2016, the entire contents of which are incorporated by reference herein. The through-wafer vias give electrical access to the back of the die where it is isolated from solution and easy to make electrical connection using any of a variety of techniques. Using through-wafer vias makes the front side of the sensor die planar, so that the sensor die can be mounted over the channel. The planar sensor die can be clamped or otherwise secured to the microfluidic chip, such as in a manner as described in U.S. patent application Ser. No. 15/482,277 filed on Apr. 7, 2017, the entire contents of which are hereby incorporated by reference.

Figure 1:
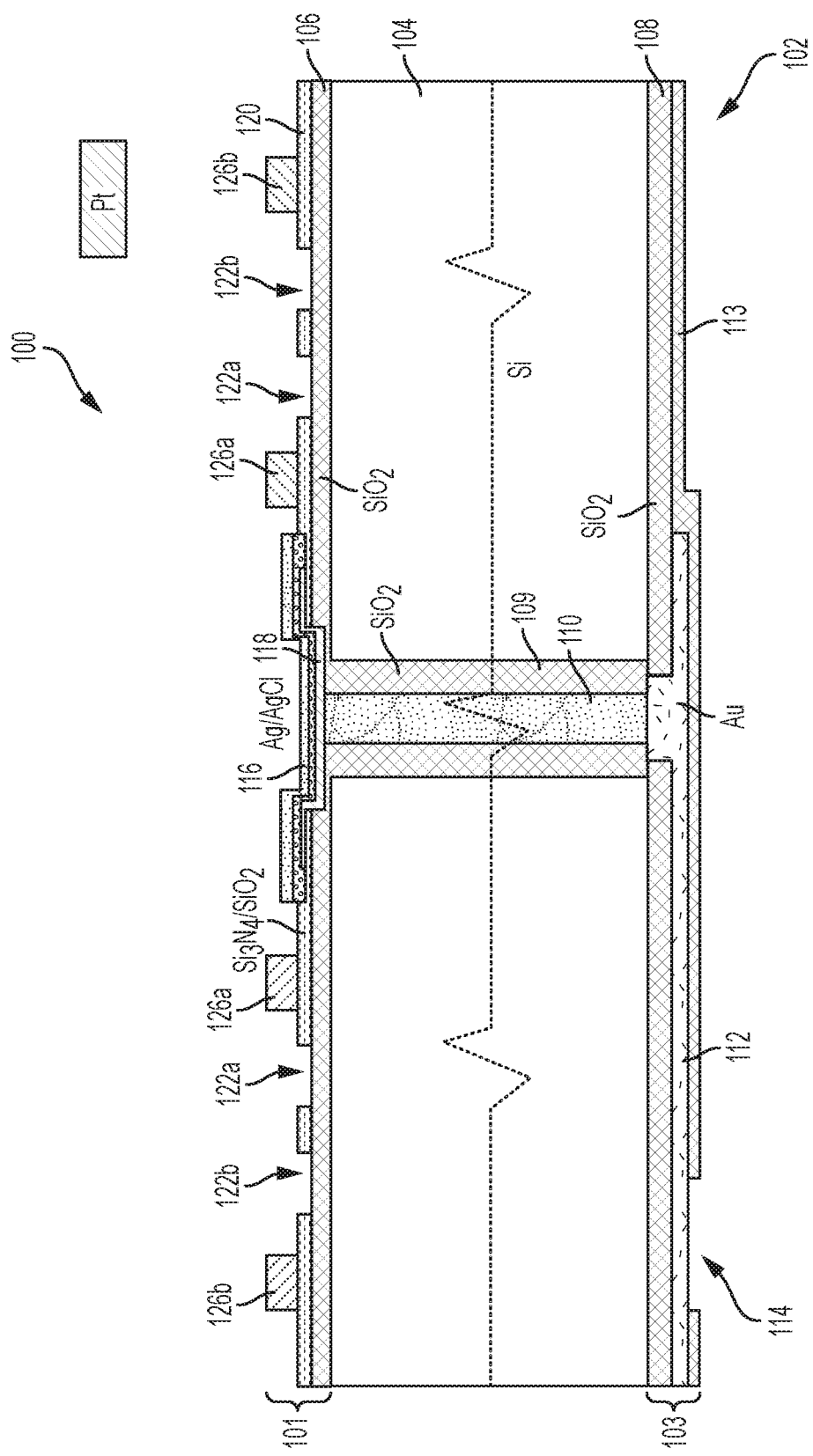
FIG. 1 is a schematic diagram of a sensor device in accordance with embodiments of the present disclosure.

FIG. 1 is a schematic diagram of a sensor device 100 in accordance with embodiments of the present disclosure. The schematic diagram shown in FIG. 1 is not drawn to scale. Sensor device 100 includes a substrate 102. Substrate 102 can include silicon 104, such as silicon <100>. The substrate 102 includes a "sensor-side" 101 and a "backside" 103. The sensor-side 101 can include a sensor-side first passivation layer 106, which can be a silicon dioxide ($SiO_2$) layer 106. The substrate backside 103 can also include a backside passivation layer 108, which can be silicon dioxide 108. The term "layer" is used throughout this disclosure and is meant to include one or more layers of a material, and is not limited to meaning a monolayer or single atomic layer of a material.

The silicon substrate 102 can be doped to make it conductive, and can include an electrically isolated doped region 110. The electrically isolated doped region 110 can include a p-type dopant, such as a boron p-type dopant. The sensor device 100 includes sensor-side electrode 116 and a backside electrode 112. The electrically isolated doped region 110 can electrically connect the sensor-side electrode 116 with the backside electrode 112 and can be electrically isolated from the rest of the substrate by a passivation layer (e.g., SiO2 layer 109). This electrically isolated doped region 110 can be referred to as a via 110 (which can be a through-silicon via 110).

The backside electrode 112 can include a conductive material, such as a metal. In some embodiments, the backside electrode 112 may include gold (Au). The backside electrode 112 can be accessed by a bonding pad 114. In some embodiments, another backside passivation layer 113 can be deposited over the backside electrode to protect the backside 103 from damage. The backside passivation layer 113 can include silicon nitride or silicon dioxide.

The sensor-side 101 can include a sensor-side electrode 116. The via 110 is physically and electrically connected to the sensor-side electrode 116. The sensor-side electrode can include silver (Ag) and silver chloride (AgCl). Silver chloride has a stable interfacial potential to the internal filling solution and it has desirable Ohmic properties.

In some embodiments, the via 110 is electrically and physically connected to a thin platinum disc 118. The platinum disc 118 can be completely covered by silver. The silver has a chloridized surface, resulting in a silver/silver-chloride electrode.

On the sensor-side first passivation layer 106, is a sensor-side second passivation layer 120. The sensor-side second passivation layer 120 can include silicon nitride ($Si_3N_4$) and silicon dioxide ($SiO_2$). As an example, the sensor-side second passivation layer 120 can be silicon nitride, or can include a layer of silicon dioxide on top of silicon nitride.

In some embodiments, adjacent to the sensor-side electrode 116 is a polyimide ring structure 126a residing on the sensor-side second passivation layer 120. The polyimide ring 126a can be circular or substantially circular, and surround the sensor-side electrode 116.

A gripping trench 122a can be etched into the sensor-side second passivation layer 120 adjacent to the polyimide ring structure 126a. The gripping trench 122a can be a first gripping trench 122a; multiple gripping trenches, such as the second gripping trench 122b can be formed adjacent to the first gripping trench 122a. The first and second gripping trenches 122a and 122b can be circular or substantially circular and can surround the sensor-side electrode 116 (and in some embodiments, surround the polyimide ring 126a).

The gripping trenches 122a and 122b can be etched to stop on the underlying sensor-side first passivation layer 106 (i.e., the silicon dioxide 106). The shape of the gripping trenches 122a and 122b prevent the membrane from pulling toward the center of the sensor when the membrane hydrates, creating osmotic pressure in the internal filling solution.

In some embodiments, a second polyimide ring 126b can reside on the sensor-side second passivation layer 120. The second polyimide ring 126b can be circular or substantially circular and can surround the sensor-side electrode 116 and the gripping trench 122a (and 122b or others, if present).

Though described as a silicon substrate, substrate 102 could in some embodiments be composed of glass or ceramic or other suitable material.

Figure 2A:
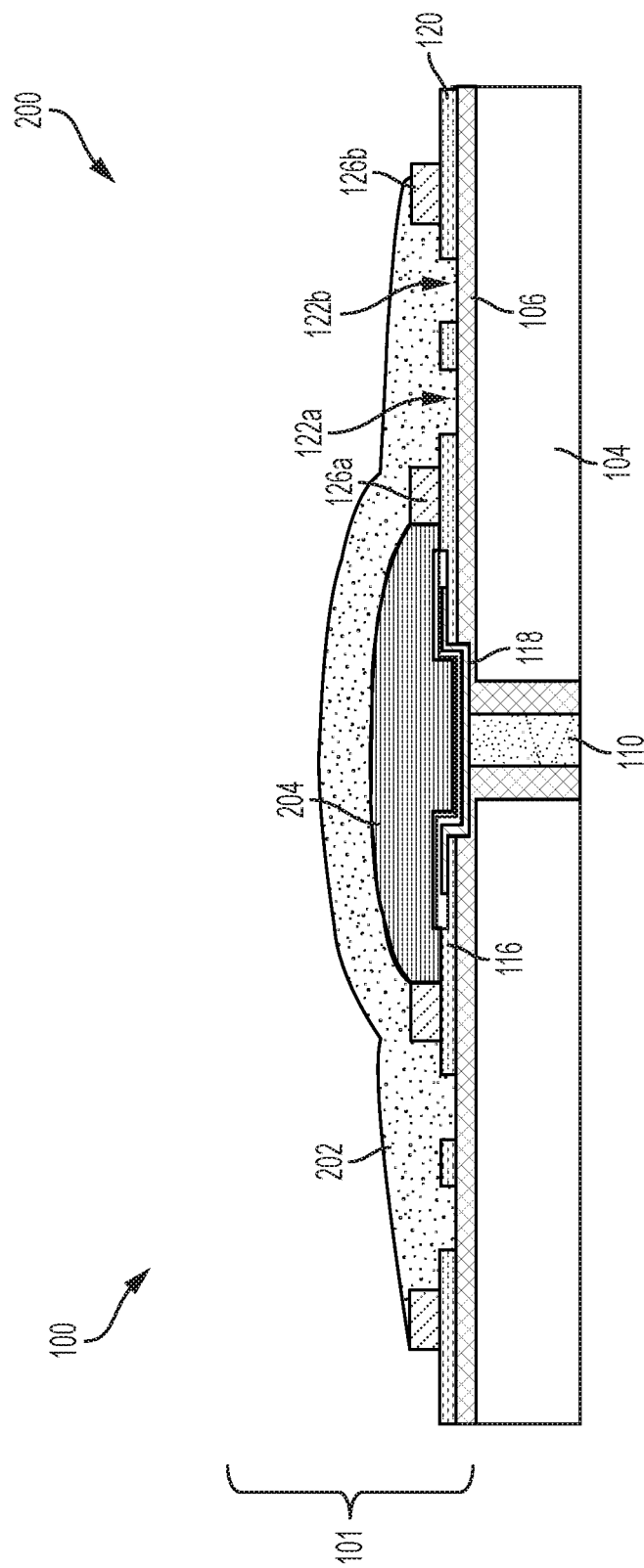
FIG. 2A is a schematic diagram of a sensor device that includes a polymeric membrane in accordance with embodiments of the present disclosure.

FIG. 2A is a schematic diagram 200 of a sensor device 100 that includes a polymeric membrane 202 in accordance with embodiments of the present disclosure. The diagram 200 of FIG. 2 shows the sensor device 100 of FIG. 1 with the addition of the polymeric membrane 202 as well as the hydrogel buffer solution 204. In FIG. 2, the first polyimide ring 126a can be shown to define the size of the hydrogel buffer solution 204. The outer polyimide ring 126b defines the size of the polymeric membrane 202 that acts as the transducer of the sensor device 100.

Also shown in FIG. 2A is the polymeric membrane 202 filling gripping trenches 122a and 122b. The polymeric membrane 202 can be "confined" by the second polyimide ring 126b based on the shape of the polyimide ring and based on surface tension of the deposited polymeric membrane cocktail solution, composed of the membrane components and organic solvent.

The polymeric membrane 202 is shown to contact the hydrogel buffer solution 204. The hydrogel buffer solution 204 can reside within the first polyimide ring 126a and contact the electrode 116. To provide a well-poised electrical contact to the polymeric membrane 202, a hydrogel buffer solution 204 can be used between the silver/silver chloride electrode 116 and the polymeric membrane 202. This hydrogel-based filling solution 204 is buffered with high concentrations of salts. The polymeric membrane 202 hydrates when exposed to aqueous solutions, and the high salt content of the hydrogel buffer solution 204 can generate considerable osmotic pressure on the polymeric membrane 202 as water moves through the membrane into the hydrogel.

By avoiding the need to put bonding wires on the sensor side of the die, the via 110 allows a mechanical clamp to be used to hold the polymeric membrane tightly onto the sensor device. The mechanical clamp and the gripping trench(es) 122a (and 122b) prevent the osmotic pressure created by the hydrogel buffer solution 204 from causing the hydrogel buffer solution to leak out from under the polymeric membrane 202, forming an electrical short circuit path around the membrane.

FIG. 2B is a schematic diagram of a sensor die 250 that includes multiple sensor devices in accordance with embodiments of the present disclosure. Sensor die 250 can include a substrate 102, as described above. The substrate 102 can include multiple sensors 100. Each sensor 100 can include a membrane 202 confined by rings 126a and 126b. The membrane can cover gripping trenches 122a and 122b. A through-silicon via 110 can electrically connect the sensor 100 to a metal electrode on the substrate 102. The substrate 102 can also include a ring 252. Ring 252 can be formed to be the same or similar height as the rings 126a and 126b. Ring 252 can be a polyimide ring formed in the same or similar way as rings 126a and 126b. Ring 252 can be used as a glue stop, as described below. The sensor die 250 can include a plurality of sensors 100, and two are shown in FIG. 2B as an example.

Figure 3:
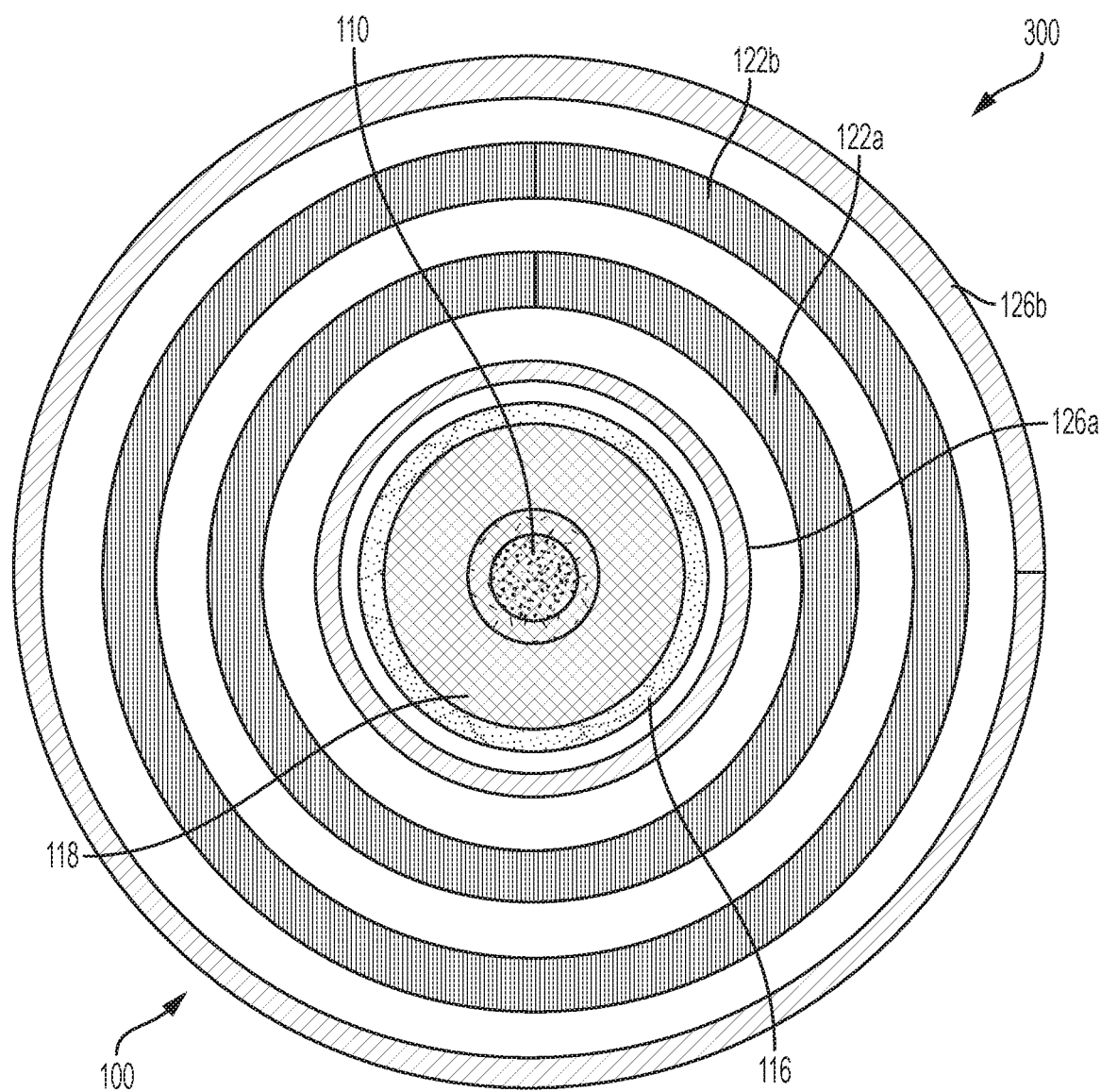
FIG. 3 is a schematic diagram of a top-down view of a sensor device in accordance with embodiments of the present disclosure.

FIG. 3 is a schematic diagram 300 of a top-down illustration of a sensor device 100 in accordance with embodiments of the present disclosure. At the center is the via 110. Above the via 110 is the platinum disk 118. Above the platinum disk 118 is the silver/silver chloride electrode 116. Around the electrode 116 is the first polyimide ring 126a. Gripping trenches 122a and 122b surround the first polyimide ring 126a. The second polyimide ring 126b surrounds the gripping trenches 122a and 122b.

Figure 4:
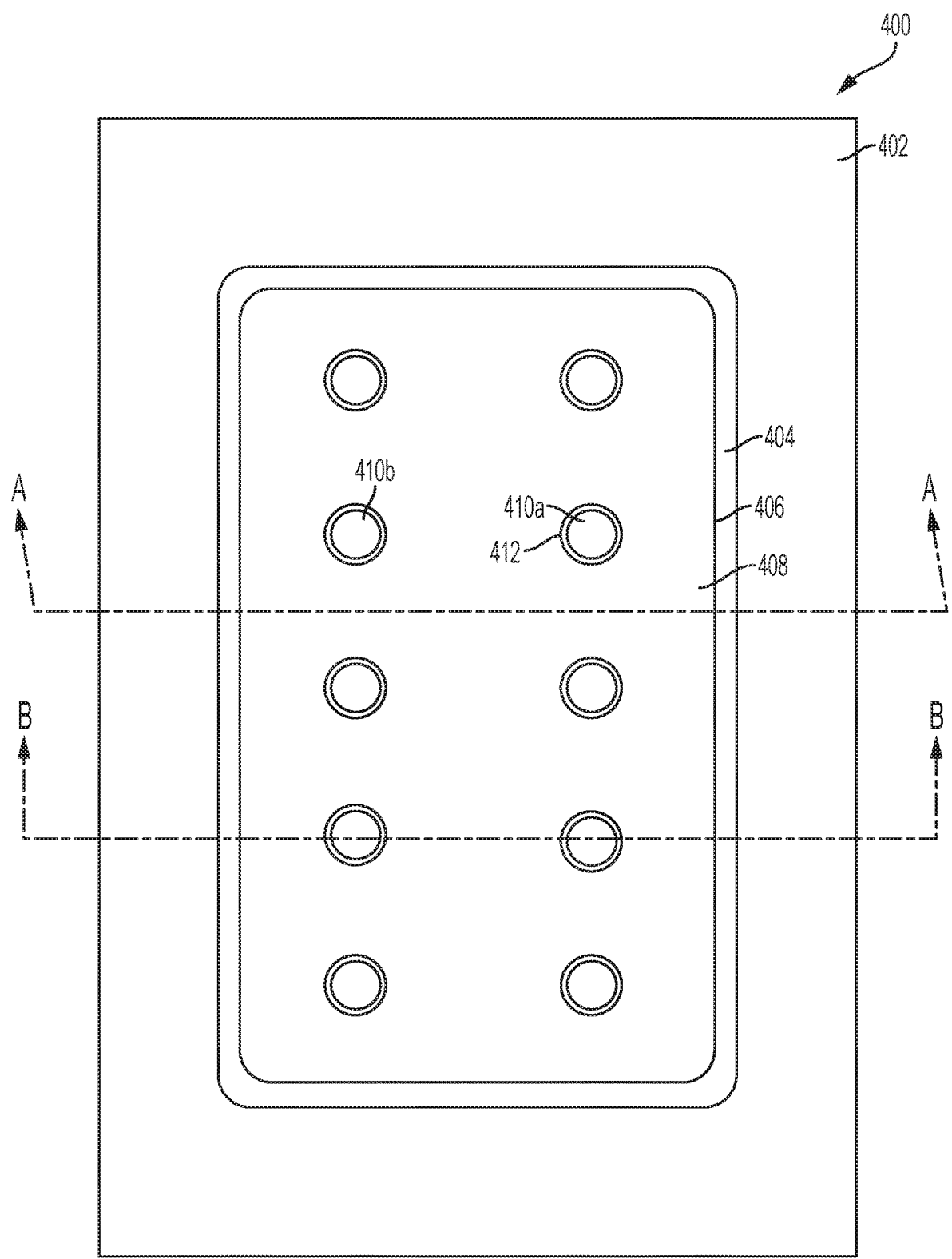
FIG. 4 is a schematic diagram of a top-down view of a portion of a microfluidic chip that includes multiple fluid channel access areas in accordance with embodiments of the present disclosure.

FIG. 4 is a schematic diagram of a top-down view of a portion of a microfluidic chip that includes multiple fluid channel access areas in accordance with embodiments of the present disclosure. The microfluidic chip sensor receiving portion 400 includes a top surface 402, a first intermediate surface 404, and a second intermediate surface 408. The first intermediate surface 404 is lower in height than the top surface 402, defining a step-wise transition from the first intermediate surface 404 to the top surface 402. The second intermediate surface 408 is lower in height than the first intermediate surface 404. The second intermediate surface 408 can include a glue stop 406. Glue stop 406 can be a raised portion extending from the second intermediate surface 408. Glue stop 406 can be substantially rectangular in shape. The glue stop 406 can have a height, such as 20 microns or similar.

The second intermediate surface 408 can include one or more sensor locations 410. Each sensor location 410 can include an opening to receive a chemical sensor device, such as sensor device 100. The second intermediate surface 408 can include a clamp bump 412 proximate to and surrounding the opening. The clamp bump 412 can have a width of about 100 microns and a height of about 10-15 microns. In some embodiments, the glue stop 406 can be taller than the clamping bump. In some embodiments, the glue stop 406 and the clamping bump 410 can have substantially the same or similar height dimensions.

The microfluidic chip sensor receiving portion 400 can have an x-dimension of (or substantially of) 3660 mm and a y-dimension of (or substantially of) 6820 mm. Ten chemical sensor locations are shown, which can be located at various locations on microfluidic chip sensor receiving portion 400. Any combination of chemical sensor locations can be used (e.g., a single sensor can be used or a plurality in any combination of locations can be used).

The microfluidic chip sensor receiving portion 400 can be made of a poly methyl methacrylate (PMMA), polycarbonate, polystyrene, or other thermoplastic polymer.

Figure 5:
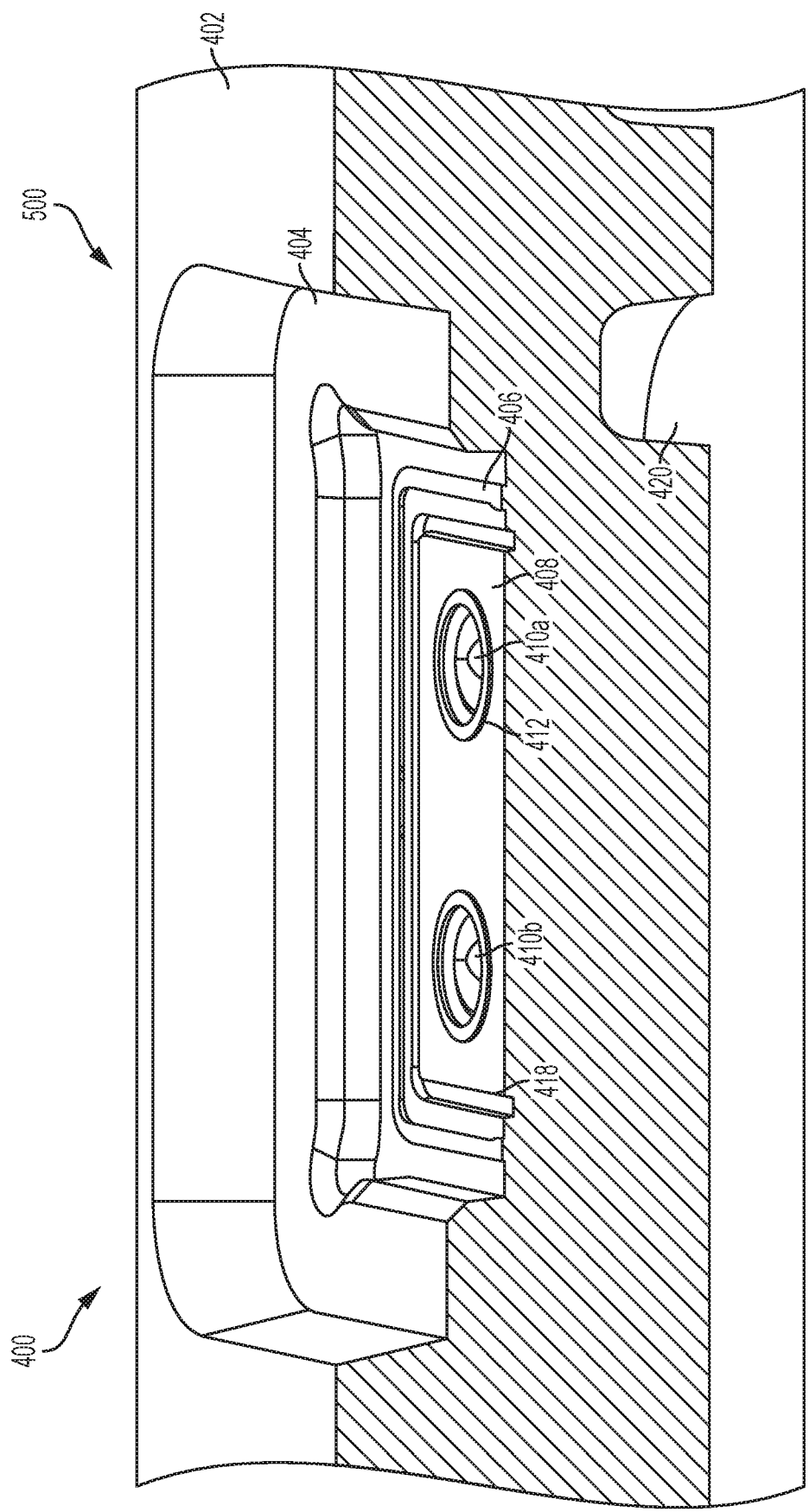
FIG. 5 is a schematic diagram of a sectional view of a portion of a microfluidic chip in accordance with embodiments of the present disclosure.

FIG. 5 is a schematic diagram of a sectional view A-A 500 of a portion of a microfluidic chip in accordance with embodiments of the present disclosure. The microfluidic chip sensor receiving portion 400 includes a top surface 402. The first intermediate surface 404 is shown as a step down from the top surface 402. In embodiments, the first intermediate surface 404 creates a glue stop and glue application point for a sensor die 250 to be clamped onto the microfluidic chip. The second intermediate surface 408 is shown as a step down from the first intermediate surface 404. The second intermediate surface 404 includes a glue stop 406 that surrounds a set of openings (e.g., opening 410a and 410b) to a microfluidic channel 420. The second intermediate surface 404 also includes a clamping bump 412 that surrounds each opening 410. In embodiments, the second intermediate surface 408 can include a trench 418 that can act as an additional glue stop. The trench 418 can be between the glue stop 406 and the set of openings.

Figure 6A:
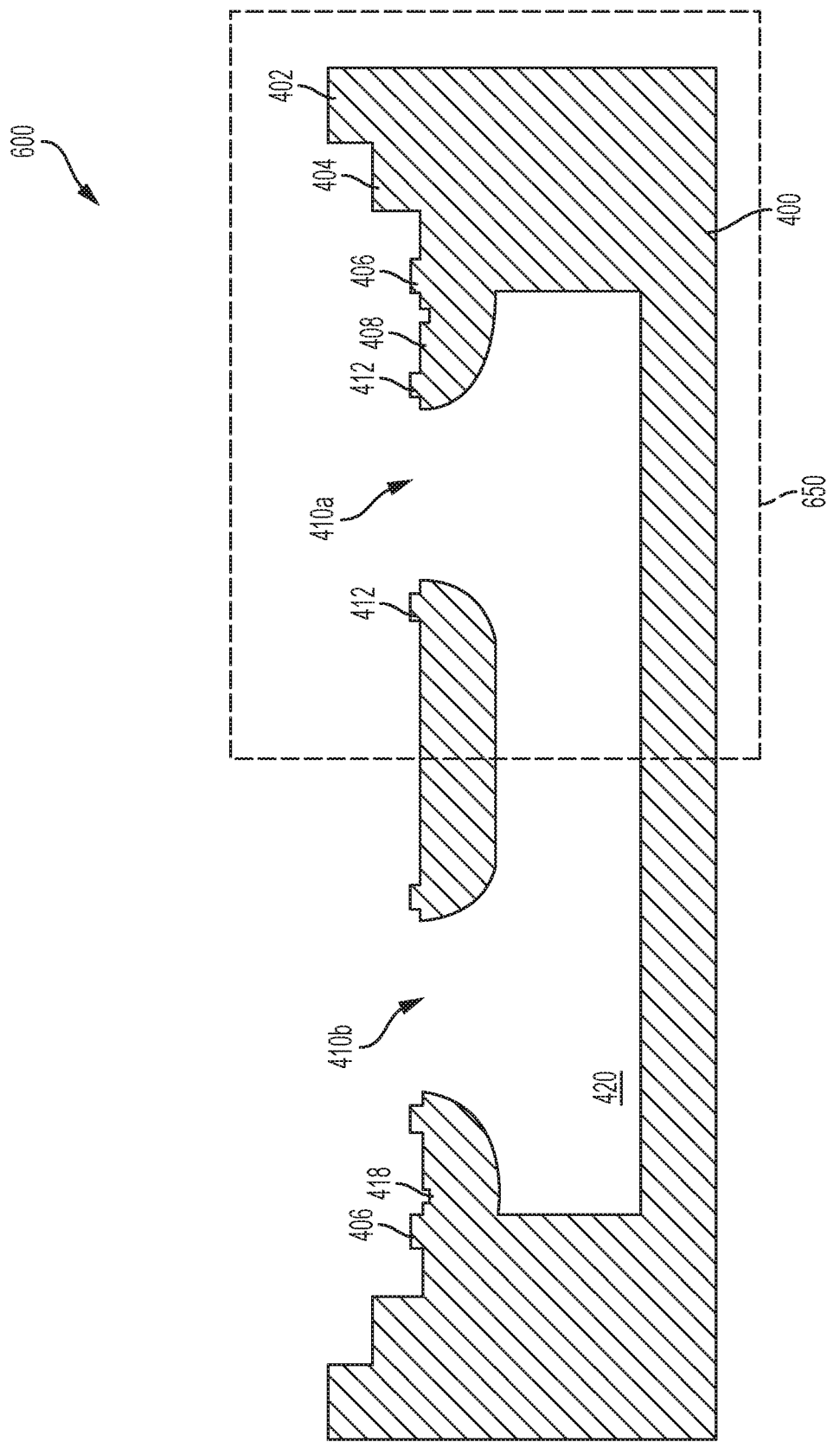
FIG. 6A is a schematic diagram of a side sectional view of a microfluidic chip in accordance with embodiments of the present disclosure.

FIG. 6A is a schematic diagram of a side sectional view B-B 600 of a microfluidic chip sensor receiving portion 400 in accordance with embodiments of the present disclosure. The side sectional view 600 illustrates the opening 410 that exposes the microfluidic channel 420. The side sectional view 600 illustrates the top surface 402, the first intermediate surface 404 stepped down from the top surface 402; and second intermediate surface 408 stepped down from the first intermediate surface 404. The glue stop 406 is shown extending from the second intermediate surface 408 and surrounding the openings 410a and 410b. The second intermediate surface 408 also includes a clamping bump 412 surrounding each opening (e.g., opening 410a). A trench 418 can be between the clamping bump 412 and the glue stop 406. The trench 418 can act as an additional glue stop for clamping the sensor die 250 onto microfluidic chip sensor receiving portion 400.

Figure 6B:
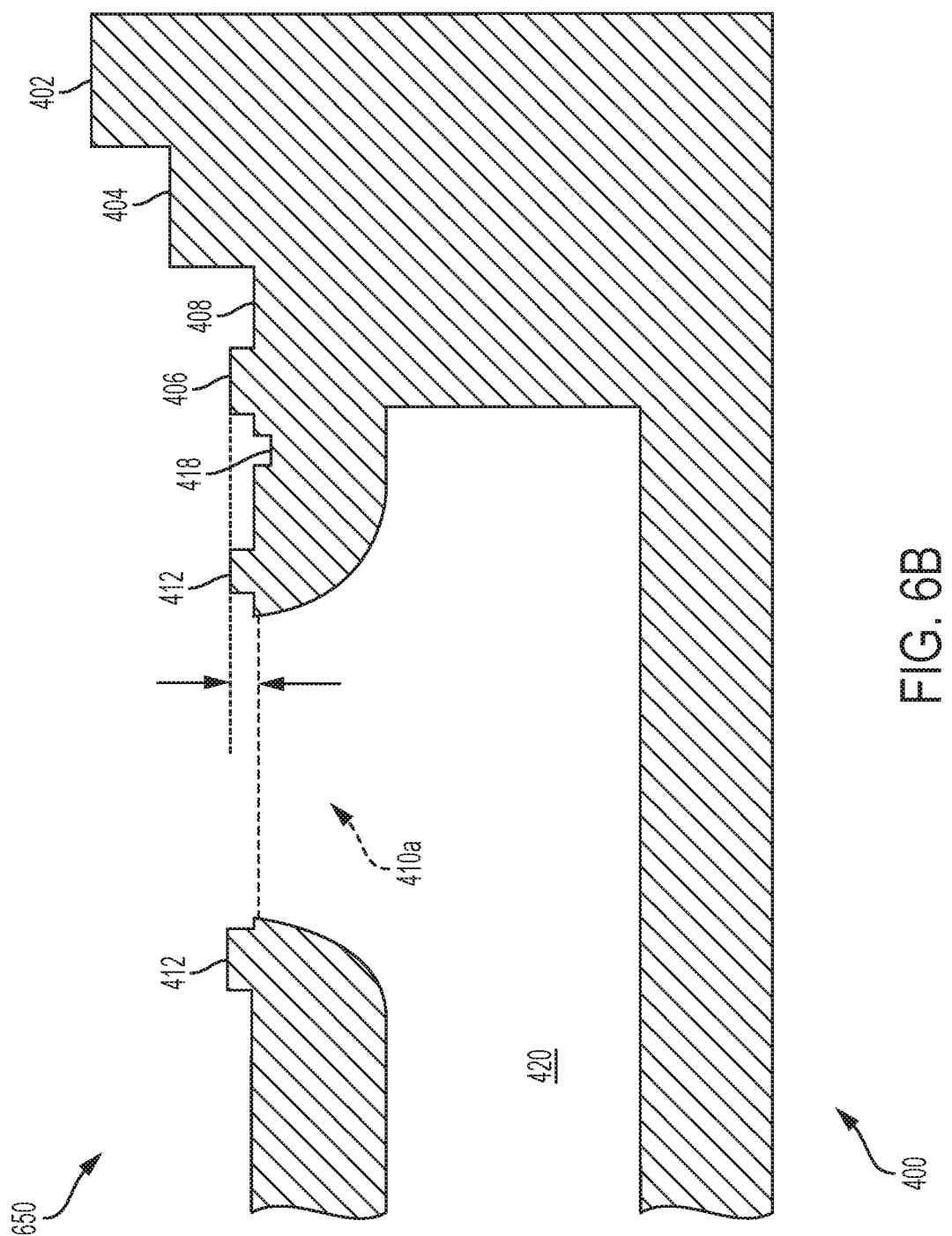
FIG. 6B is a schematic diagram of a close-up view of the microfluidic chip of FIG. 6A in accordance with embodiments of the present disclosure.

FIG. 6B is a schematic diagram of a close-up view of the microfluidic chip of FIG. 6A in accordance with embodiments of the present disclosure. As shown in FIG. 6B, the clamping bump 412 can be the same or similar height as the glue stop 406.

Figure 6C:
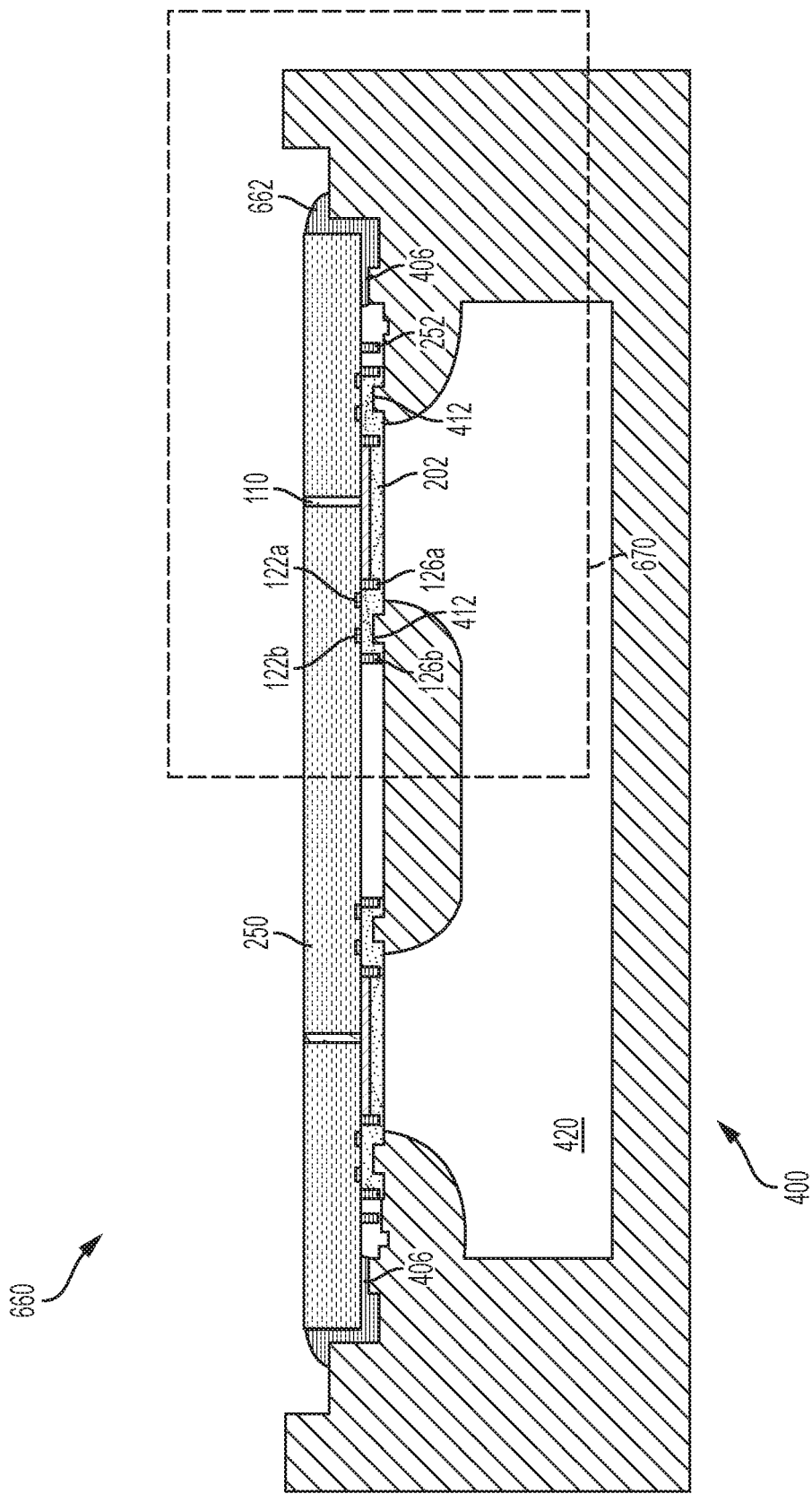
FIG. 6C is a schematic diagram of a side sectional view of a sensor die clamped to a microfluidic chip in accordance with embodiments of the present disclosure.

FIG. 6C is a schematic diagram of a side sectional view 660 of a sensor die 250 clamped to a microfluidic chip sensor receiving portion 400 in accordance with embodiments of the present disclosure. The sensor die 250 is placed onto the microfluidic chip sensor receiving portion 400 under an applied pressure. While under pressure, an adhesive 662 is applied to a gap between the first intermediate surface 404 and the second intermediate surface 408. The adhesive 662 is cured under pressure. An example adhesive is a UV-cured acrylated urethane, though other adhesives can be used. The sensors are aligned over the openings 410a and 410b. The clamping bump 412 contacts the membrane 202 in a location between rings 126a and 126b. The applied pressure can cause the membrane 202 to be compressed into the gripping trenches 122a and 122b.

Figure 6D:
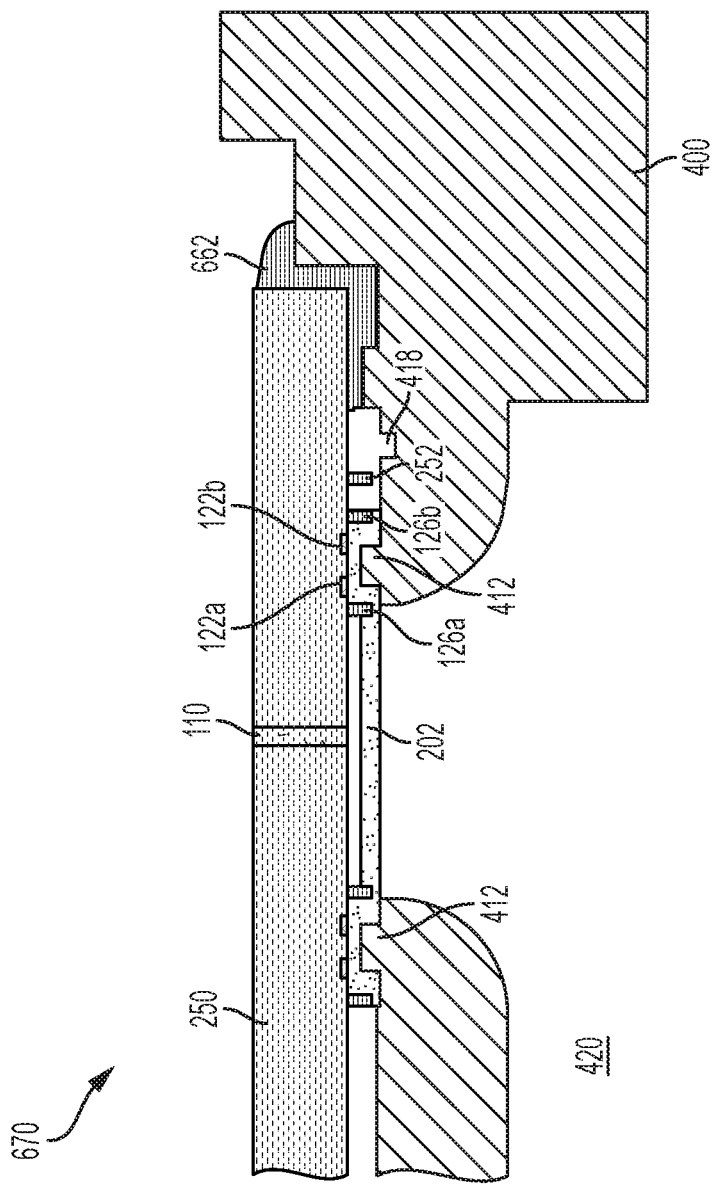
FIG. 6D is a schematic diagram of a close-up view of a sensor die clamped to the microfluidic chip of FIG. 6C in accordance with embodiments of the present disclosure.

FIG. 6D is a schematic diagram of a close-up view 670 of a sensor die 250 clamped to the microfluidic chip sensor receiving portion 400 of FIG. 6C in accordance with embodiments of the present disclosure. The close-up view 670 illustrates the clamping bump 412 in contact with the membrane 202 at a location between the rings 126a and 126b. The applied pressure of the sensor die 250 onto the clamp 412 pushes on the membrane 202 such that the membrane compresses into the trenches 122a and 122b. The close-up view 670 also illustrates the glue-stop trench 418.

Figure 7A:
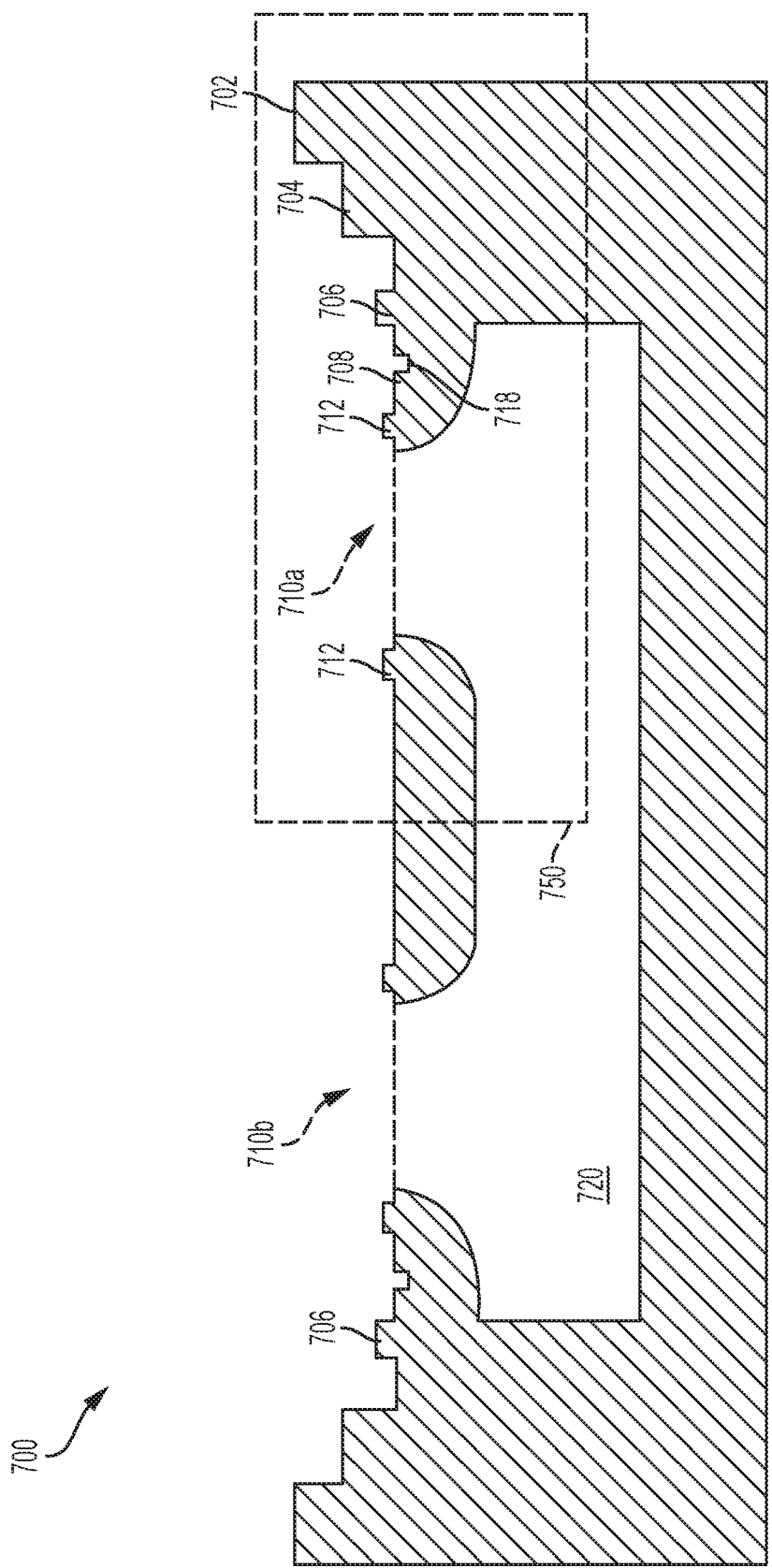
FIG. 7A is a schematic diagram of a side sectional view of a microfluidic chip in accordance with embodiments of the present disclosure.

FIG. 7A is a schematic diagram of a side sectional view of a microfluidic chip 700 in accordance with embodiments of the present disclosure. The side sectional view 700 illustrates the opening 710 that exposes the microfluidic channel 720. The side sectional view 700 illustrates the top surface 702, the first intermediate surface 704 stepped down from the top surface 702; and second intermediate surface 708 stepped down from the first intermediate surface 704. The glue stop 706 is shown extending from the second intermediate surface 708 and surrounding the openings 710a and 710b. The second intermediate surface 708 also includes a clamping bump 712 surrounding each opening (e.g., opening 710a). A trench 718 (shown in FIG. 7B) can be between the clamping bump 712 and the glue stop 706. The trench 718 can act as an additional glue stop for clamping the sensor die 250 onto microfluidic chip 700.

Figure 7B:
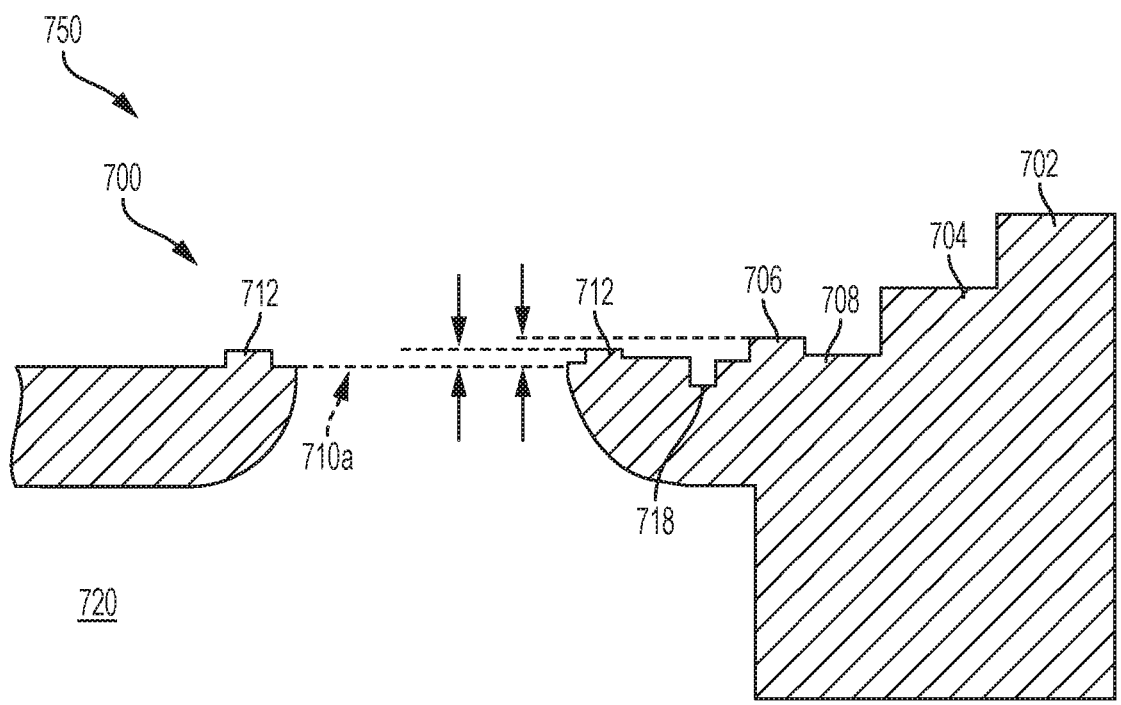
FIG. 7B is a schematic diagram of a close-up view of the microfluidic chip of FIG. 7A in accordance with embodiments of the present disclosure.

FIG. 7B is a schematic diagram of a close-up view 750 of the microfluidic chip of FIG. 7A in accordance with embodiments of the present disclosure. As shown in FIG. 7B, the clamping bump 712 can be at a lower height than the glue stop 706.

Figure 7C:
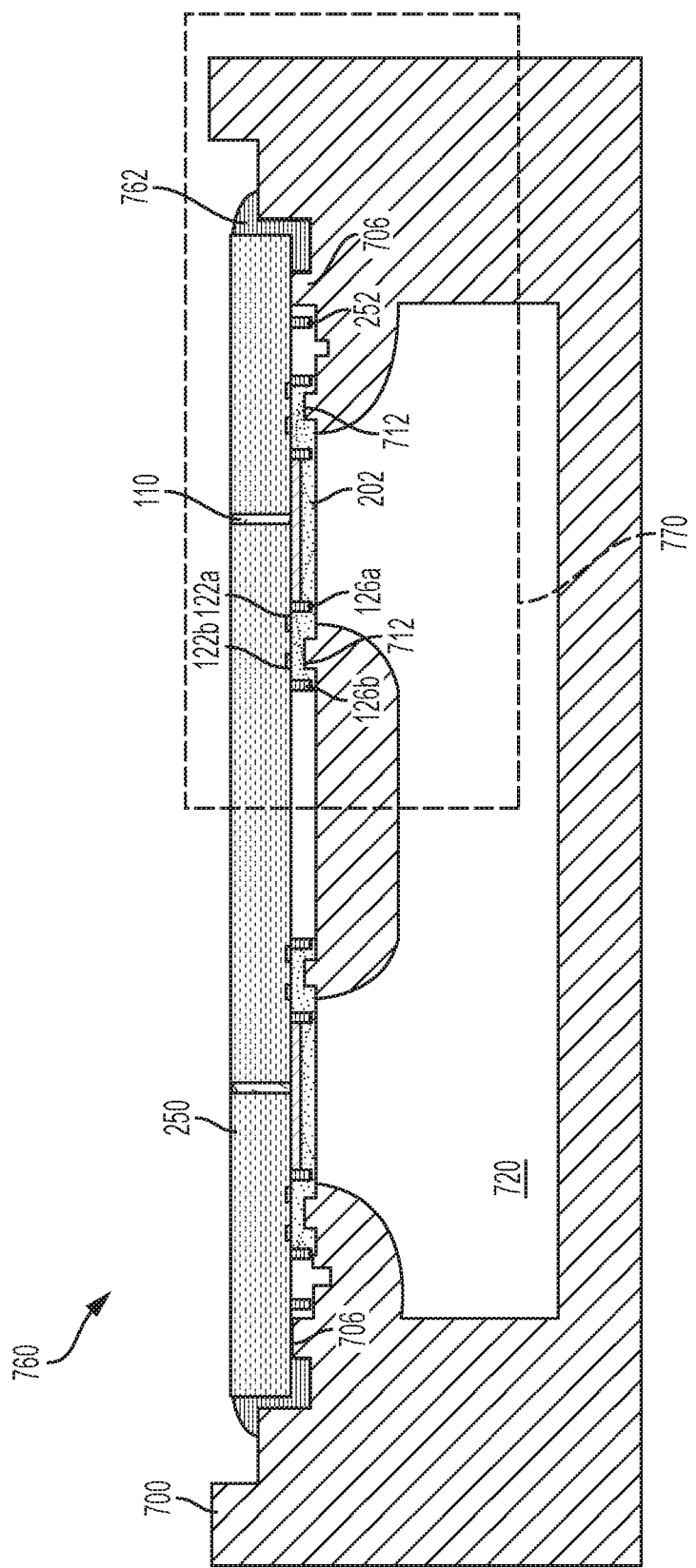
FIG. 7C is a schematic diagram of a side sectional view of a sensor die clamped to a microfluidic chip in accordance with embodiments of the present disclosure.

FIG. 7C is a schematic diagram of a side sectional view 760 of a sensor die 250 clamped to a microfluidic chip 700 in accordance with embodiments of the present disclosure. The sensor die 250 is placed onto the microfluidic chip 700 under an applied pressure. While under pressure, an adhesive 762 is applied to a gap between the first intermediate surface 704 and the second intermediate surface 708. The adhesive 762 is cured while pressure is applied to hold the die in contact with the microfluidic chip. The sensors are aligned over the openings 710a and 710b. The clamping bump 712 contacts the membrane 202 in a location between rings 126a and 126b. The applied pressure can cause the membrane 202 to compress into the gripping trenches 122a and 122b. The glue stop 706 can contact the sensor die 250 due to the glue stop 706 height being taller than the clamping bump 712. The contact made between the glue stop 706 and the sensor die 250 can further aide in preventing the adhesive 762 from contacting the membrane 202 or other parts of the sensor. Glue stop 706 can act as a spacer or hard stop for the sensor die 250.

Figure 7D:
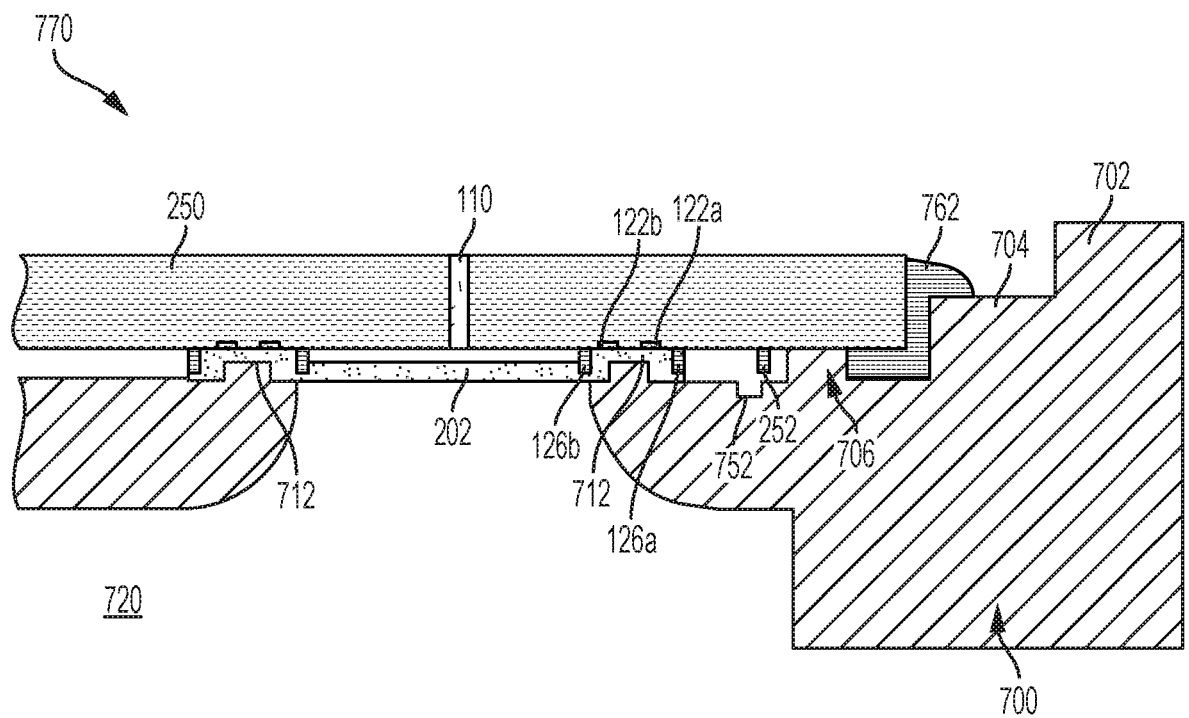
FIG. 7D is a schematic diagram of a close-up view of a sensor die clamped to the microfluidic chip of FIG. 7C in accordance with embodiments of the present disclosure.

FIG. 7D is a schematic diagram of a close-up view 770 of a sensor die 250 clamped to the microfluidic chip 700 of FIG. 7C in accordance with embodiments of the present disclosure. The close-up view 770 illustrates the clamping bump 712 in contact with the membrane 202 at a location between the rings 126a and 126b. The applied pressure of the sensor die 250 onto the clamp 712 pushes on the membrane 202 such that the membrane compresses into the trenches 122a and 122b. The close-up view 770 also illustrates the glue-stop trench 718.

Figure 8A:
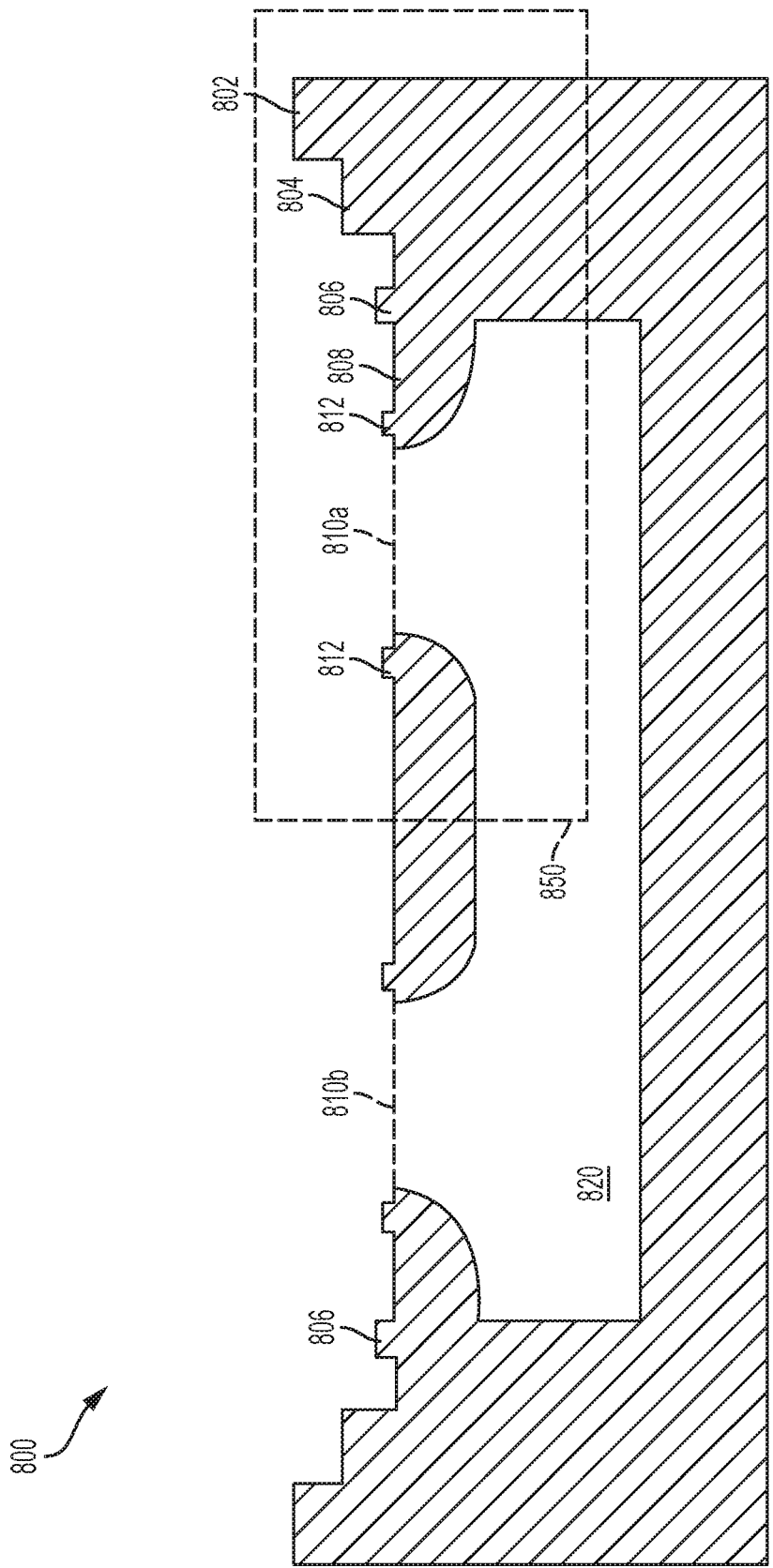
FIG. 8A is a schematic diagram of a side sectional view of a microfluidic chip in accordance with embodiments of the present disclosure.

FIG. 8A is a schematic diagram of a side sectional view of a microfluidic chip 800 in accordance with other embodiments of the present disclosure. The microfluidic chip 800 includes an opening 810 that exposes the microfluidic channel 820. The side sectional view 800 illustrates the top surface 802, the first intermediate surface 804 stepped down from the top surface 802; and second intermediate surface 808 stepped down from the first intermediate surface 804. The glue stop 806 is shown extending from the second intermediate surface 808 and surrounding the openings 810a and 810b. The second intermediate surface 808 also includes a clamping bump 812 surrounding each opening (e.g., opening 810a). The microfluidic chip 800 does not include a trench between the glue stop 806 and the clamping bump 812.

Figure 8B:
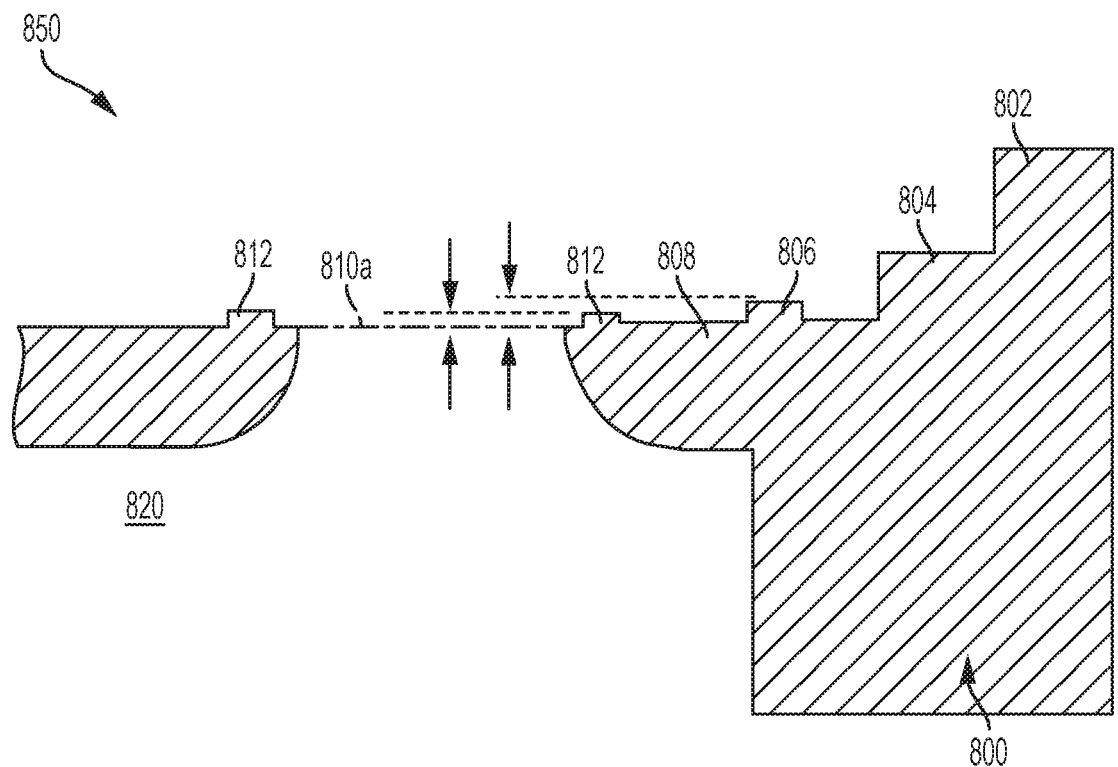
FIG. 8B is a schematic diagram of a close-up view of the microfluidic chip of FIG. 8A in accordance with embodiments of the present disclosure.

FIG. 8B is a schematic diagram of a close-up view 850 of the microfluidic chip of FIG. 8A in accordance with embodiments of the present disclosure. As shown in FIG. 8B, the clamping bump 812 can be at a lower height than the glue stop 806.

Figure 9A:
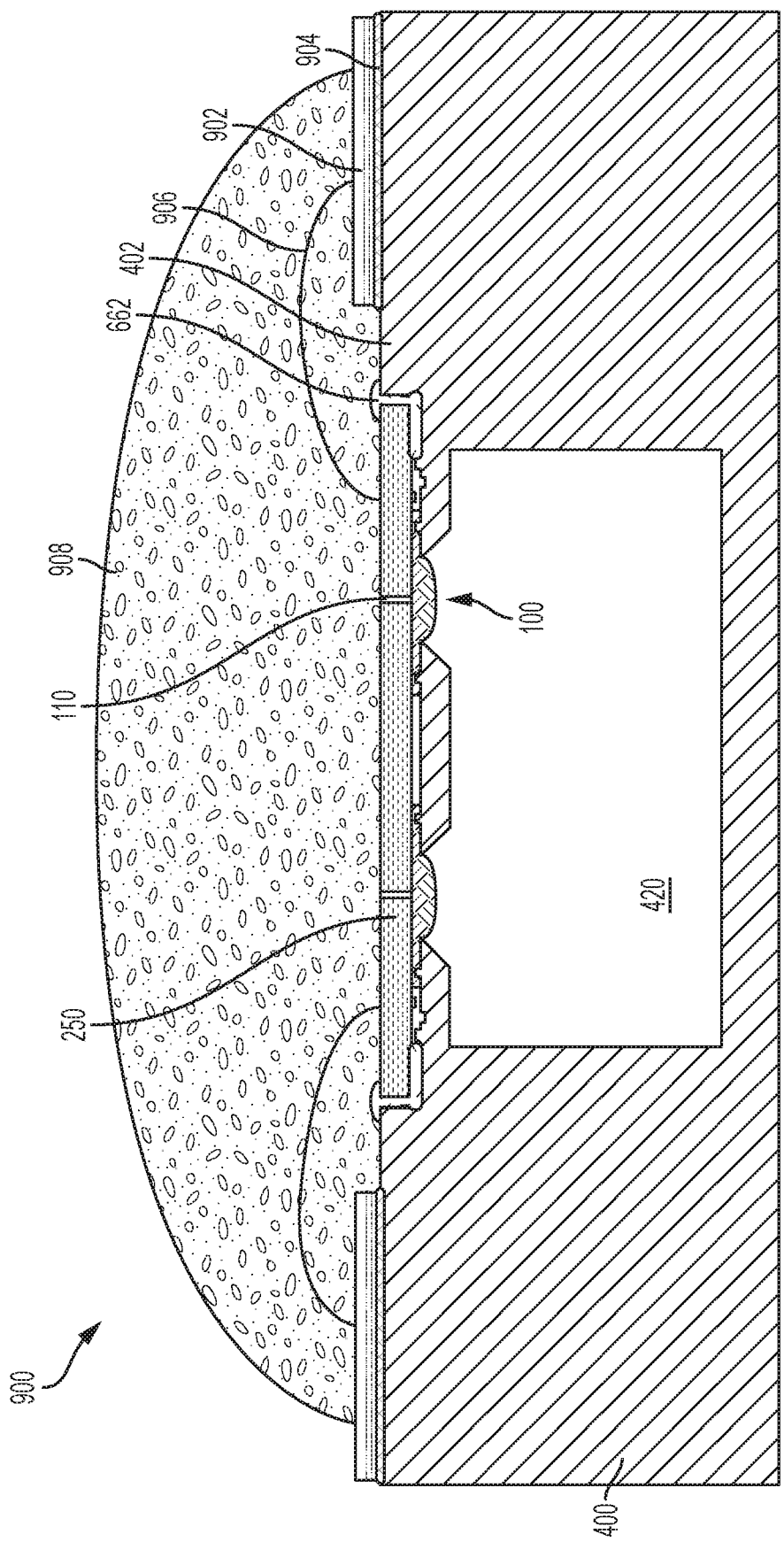
FIG. 9A is a schematic diagram of a side sectional view of a sensor die clamped to a microfluidic chip and electrically coupled to a printed circuit board in accordance with embodiments of the present disclosure.
Figure 9B:
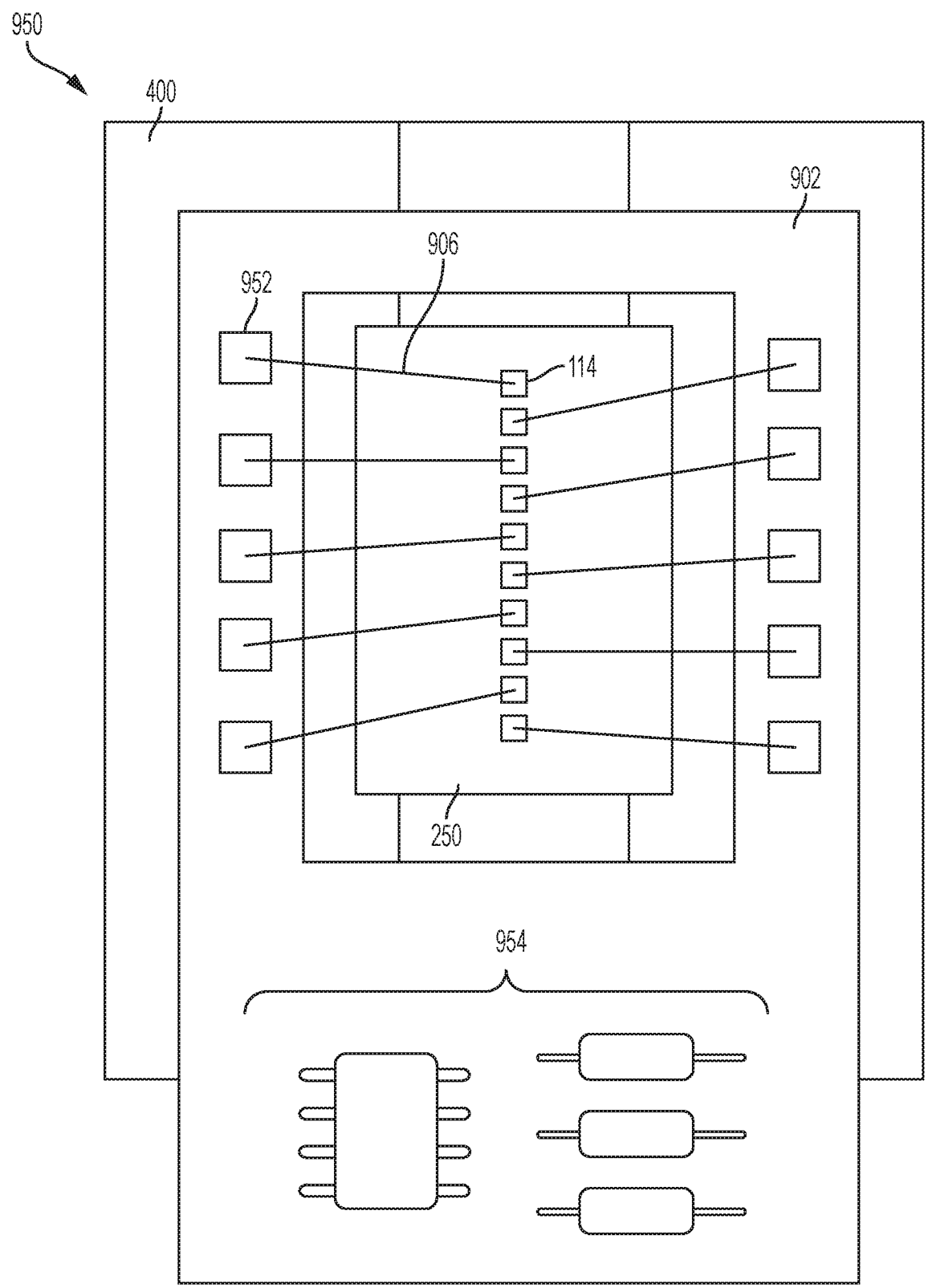
FIG. 9B is a schematic diagram of a top-down view of the sensor die clamped to a microfluidic chip and electrically coupled to a printed circuit board of FIG. 9A in accordance with embodiments of the present disclosure.

FIG. 9A is a schematic diagram of a side sectional view 900 of a sensor die 250 clamped to a microfluidic chip sensor receiving portion 400 and electrically coupled to a printed circuit board 902 in accordance with embodiments of the present disclosure. Microfluidics chip 400 is similar to microfluidics chip 400 shown in FIGS. 4-6D, but can also be similar to microfluidic chip 700 of FIGS. 7A-7D or microfluidic chip 800 of FIGS. 8A-B. The sensor die 250 is clamped to the microfluidic chip sensor receiving portion 400 by an adhesive (such as adhesive substance 662 or adhesive substance 762) that is applied while the sensor die 250 is pushed down onto the microfluidic chip sensor receiving portion 400 and cured. A printed circuit board 902 can be adhered to the top surface 402 of the microfluidic chip sensor receiving portion 400 by an adhesive 904. Adhesive 904 can be an adhesive tape, double sided tape, glue, or other known technique of affixing a rigid structure onto the microfluidic chip sensor receiving portion 400. The printed circuit board 902 can include one or more contact pads 952 (shown in FIG. 9B) that are electrically connected to other circuit elements 954 (some of which are represented in FIG. 9B) through conductive traces (not shown). Each sensor 100 can be electrically connected to the printed circuit board 902 via wire bonds 906. After wire bonding has been completed, an encapsulant 908 can be applied over at least a portion of the printed circuit board 902 to protect the wire bond 906 and to electrically insulate the contact pads. The encapsulant can be a UV-cured modified urethane.

The printed circuit board 902 can be generalized to include a rigid structure, which can be used to provide electrical connectivity between the sensor 100 and outside electronics. The rigid structure can be a PCB, a metal surface, a polymer surface, etc.

FIG. 9B is a schematic diagram of a top-down view 950 of the sensor die clamped to a microfluidic chip and electrically coupled to a printed circuit board of FIG. 9A in accordance with embodiments of the present disclosure. FIG. 9B illustrates the sensor die 250 that includes sensor contacts 114. Sensor contacts 114 are electrically connected to the ISE of the sensor through a via 110 (shown in FIG. 9A). The sensor contacts 114 are electrically connected to contact pads 952 on PCB 902 via wire bonds 906. As shown, the PCB 902 can also include electrical components 954 that can perform various functions including applying bias to the sensor, detecting electrical signals from the sensor, and other functions.

FIG. 10A is a schematic diagram of a side sectional view 1000 of a sensor die 250 clamped to a microfluidic chip sensor receiving portion 400 and secured to the microfluidic chip by screws 1004 in accordance with embodiments of the present disclosure. A rigid structure 1002 can be used to provide electrical connectivity between the sensor 100 and outside electronics. The rigid structure 1002 can be a PCB, a metal surface, a polymer surface, etc. The microfluidic chip sensor receiving portion 400 and the rigid structure 1002 can include through holes for receiving screws 1004, which are secured using a locking nut in this embodiment.

Figure 10B:
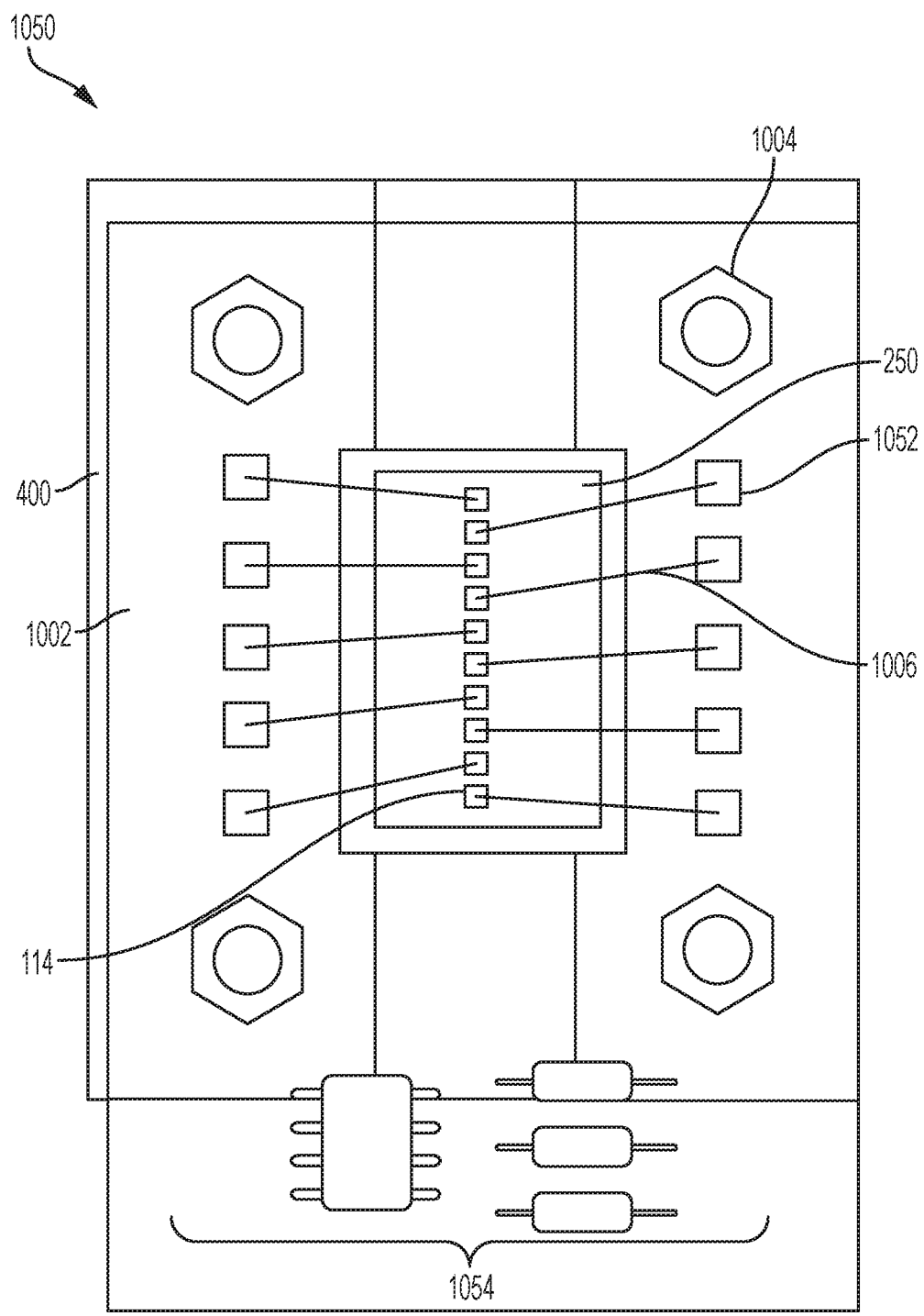
FIG. 10B is a schematic diagram of a top-down view of a sensor die clamped to a microfluidic chip of FIG. 10A in accordance with embodiments of the present disclosure.

FIG. 10B is a schematic diagram of a top-down view 1050 of a sensor die 250 clamped to a microfluidic chip sensor receiving portion 400 of FIG. 10A in accordance with embodiments of the present disclosure. FIG. 10A illustrates the rigid structure 1002 to include contact pads 1052 that can electrically connect contacts 114 on the sensor to outside electronics (e.g., electronics 1054) via a wire bond 1006. The screws 1004 are shown to secure the rigid structure 1002 to the microfluidic chip sensor receiving portion 400 with nuts on the underside, not shown.

Figure 11A:
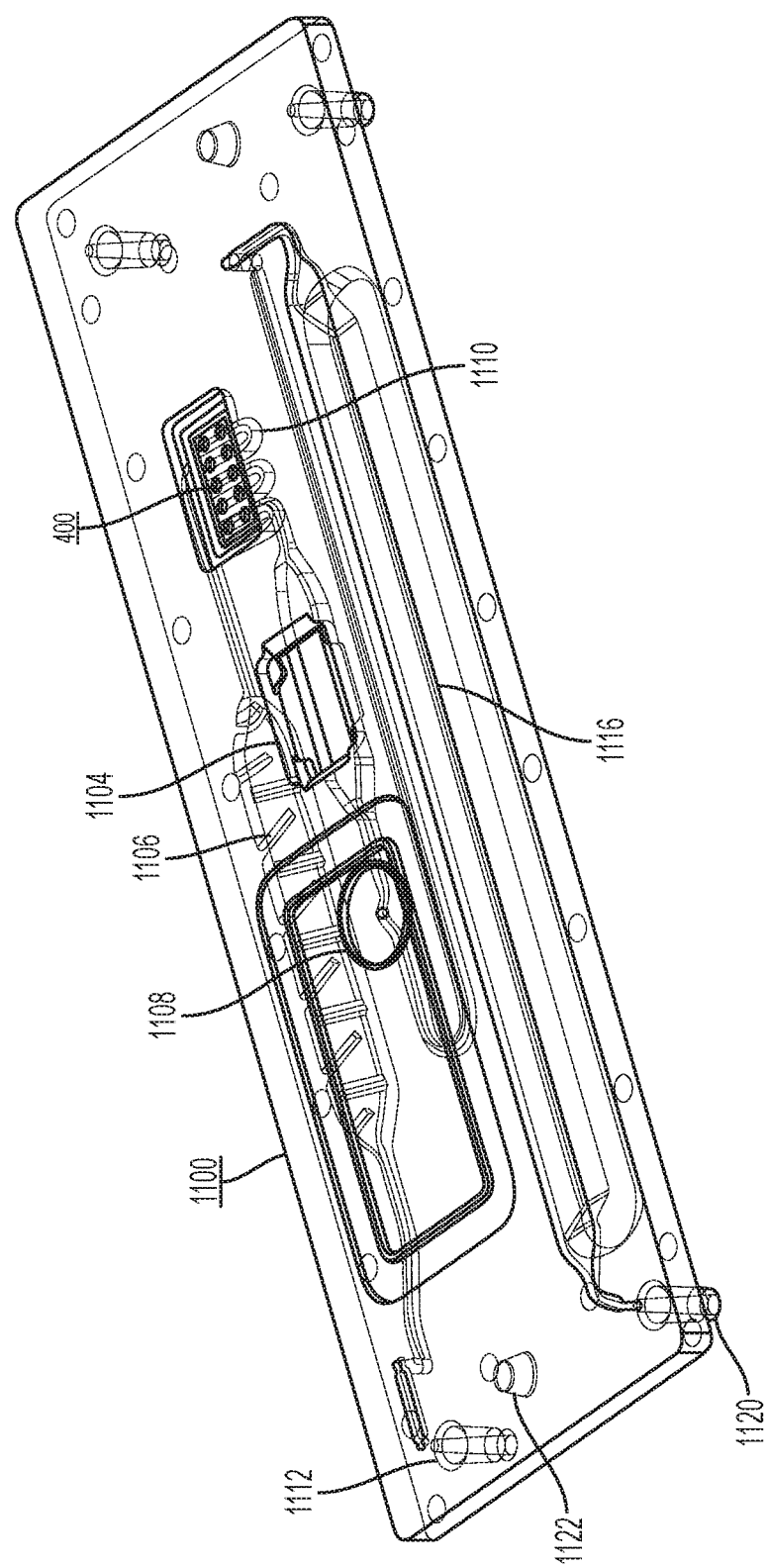
FIG. 11A is a schematic diagram of a microfluidic chip in accordance with embodiments of the present disclosure.

FIG. 11A is a schematic diagram of a microfluidic chip 1100 in accordance with embodiments of the present disclosure. The microfluidic chip 1100 can be made of a poly methyl methacrylate (PMMA), polycarbonate, polystyrene, or other thermoplastic polymer. The microfluidic chip 1100 can include a microfluidic chip sensor receiving portion 400, as described above. The microfluidic chip 1100 can include a fluid inlet 1112. The fluid inlet 1112 is disposed on a bottom side of the microfluidic chip 1100. The fluid inlet 1112 can receive a fluid and direct the fluid towards a microfluidic channel 1152, shown in FIG. 11B. The microfluidic chip 1100 can also include a mixing chamber 1106 downstream of the fluid inlet 1112. The mixing chamber 1106 can include a plurality of fingers or baffles that can cause the inlet fluid to change directions multiple times as the fluid flows through the mixing chamber 1106.

The microfluidic chip 1100 can include a microfluidic chip sensor receiving portion 400. The microfluidic chip sensor receiving portion 400 can receive a microfluidic sensor die, such as sensor die 250. The microfluidic channel 1110 shown in FIG. 11A can be serpentine shaped channel that directs fluid across each sensor location of the microfluidic chip sensor receiving portion 400. In embodiments, such as that shown in FIG. 11B, the microfluidic channel 1152 is a straight channel. Both structures of channel are within the scope of this disclosure. The microfluidic chip sensor receiving portion 400 can receive a potentiometric sensor, such as sensor 100. The microfluidic chip sensor receiving portion 400 is discussed in more detail in the text accompanying FIG. 15.

Downstream of the microfluidic chip sensor receiving portion 400 is an amperometric sensor receiving area 1104.

Figure 14:
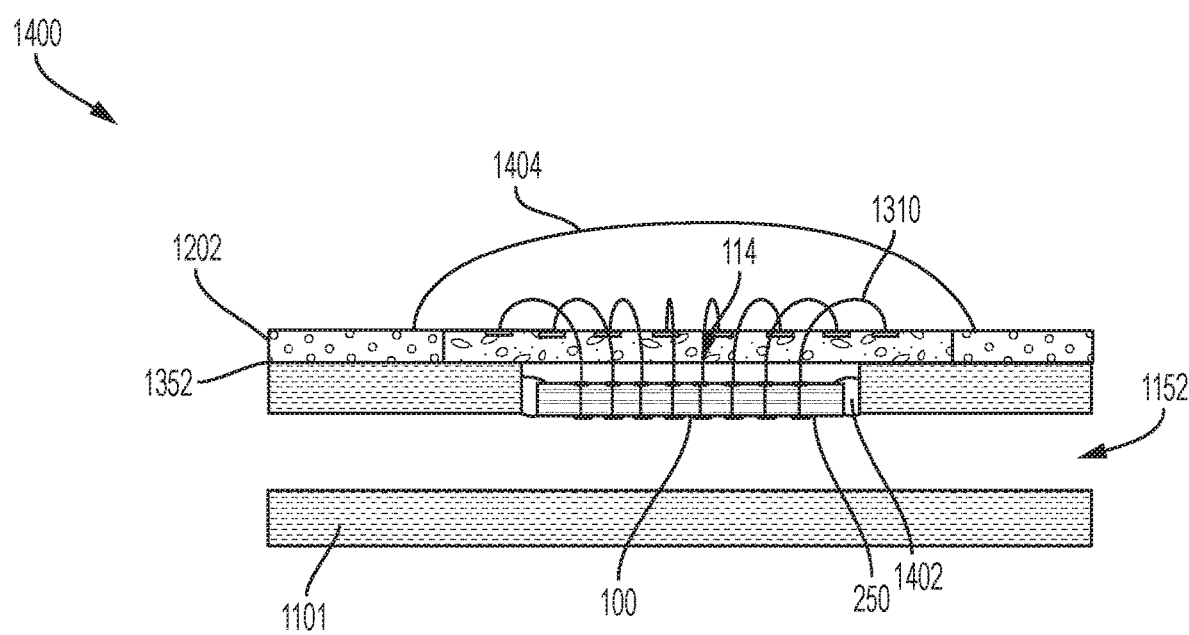
FIG. 14 is a close-up view of the side, cut away view of the assembled microfluidic chip showing a sensor die with a fully exposed sensor area in accordance with embodiments of the present disclosure.

The amperometric sensor receiving area 1104 is discussed in more detail in the text accompanying FIG. 14.

Downstream of the amperometric sensor receiving area 1104 is a reference electrode receiving area 1108. The reference electrode receiving area 1104 is discussed in more detail in the text accompanying FIG. 16.

Downstream of the reference electrode receiving area 1104 is a turbidity sensor area 1116. Downstream of the turbidity sensor area 1104 is a fluid outlet 1120.

The microfluidic chip 1100 includes one or more PCB alignment structures 1122. The PCB alignment structure 1122 can be a protrusion that can pass through a hole in the PCB to align the PCB with the microfluidic chip 1100.

Figure 11B:
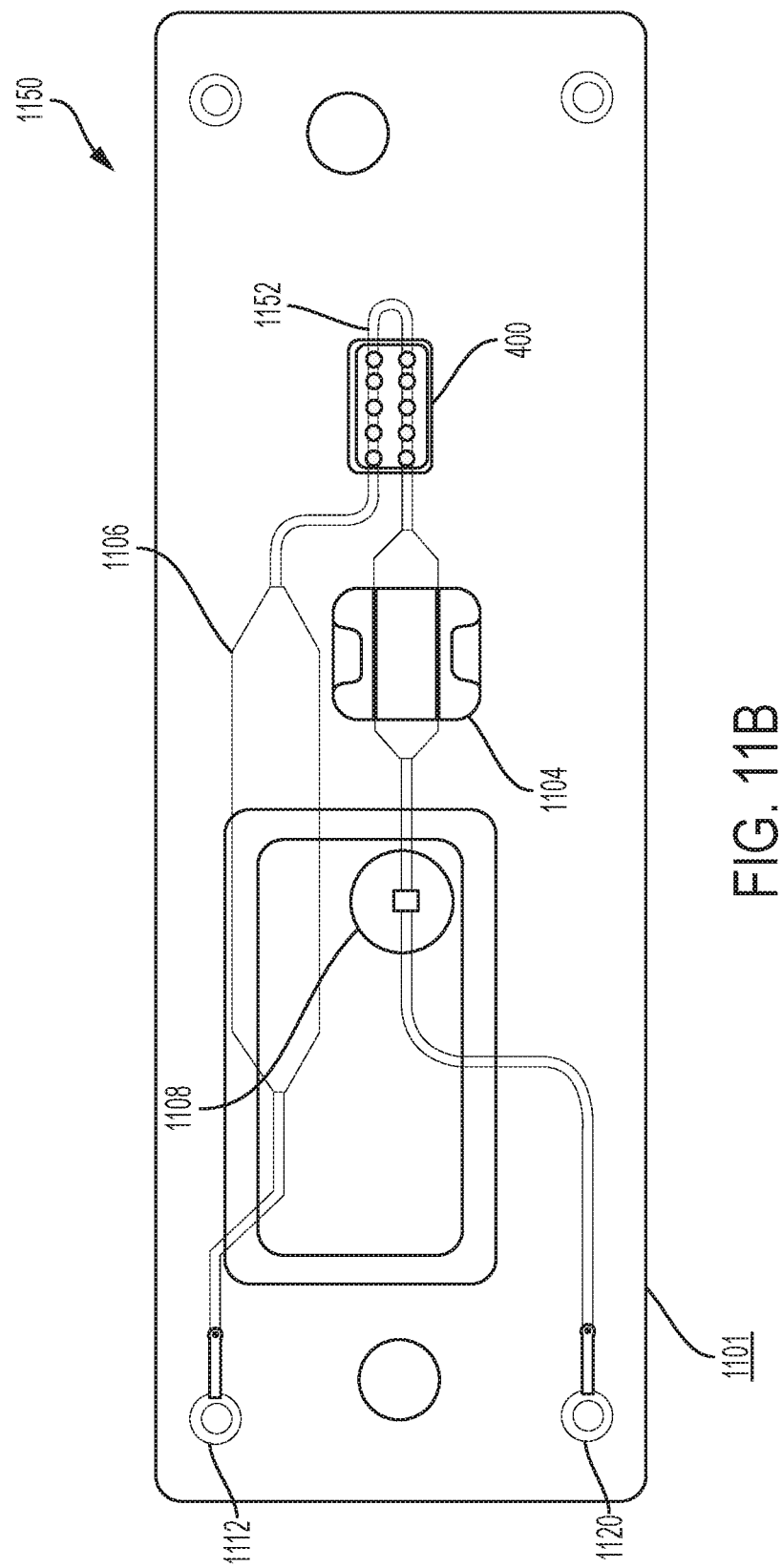
FIG. 11B is a top-down view of a schematic diagram of a microfluidic chip in accordance with embodiments of the present disclosure.

FIG. 11B is a top-down view 1150 of a schematic diagram of a microfluidic chip 1101 in accordance with embodiments of the present disclosure. Microfluidic chip 1101 is similar to microfluidic chip 1100, but is shown to include a non-serpentine shaped microfluidic channel 1152 in the region corresponding to the microfluidic chip sensor receiving portion 400. The top-down view 1150 of the microfluidic chip 1101 illustrates example positions of the microfluidic chip sensor receiving portion 400, the amperometric sensor area 1104, and the reference electrode area 1108, as well as corresponding microfluidic channel 1152 for each of the sensor areas.

Figure 12:
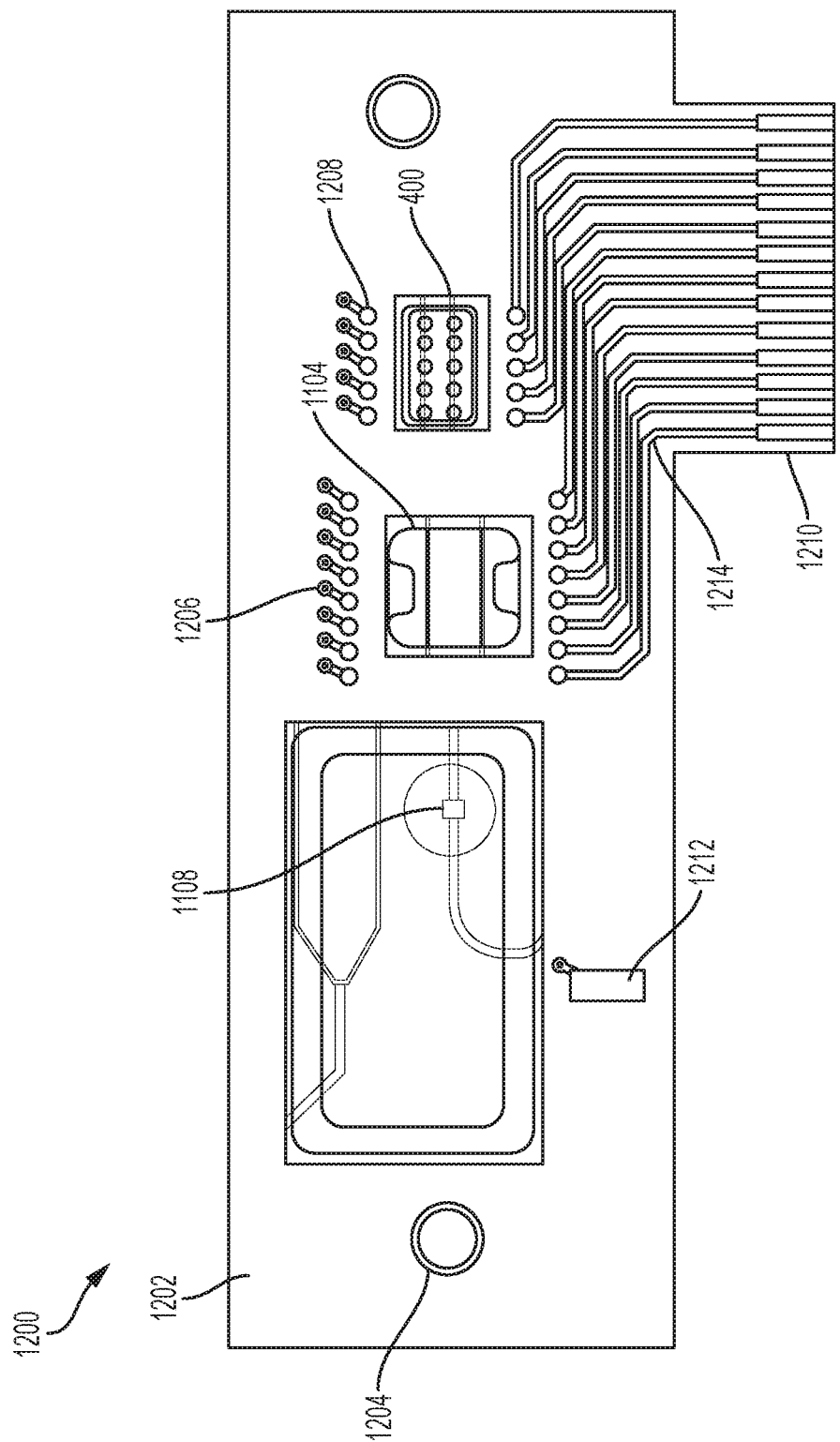
FIG. 12 is a schematic diagram of microfluidic chip that includes a printed circuit board in accordance with embodiments of the present disclosure.

FIG. 12 is a schematic diagram 1200 of microfluidic chip 1101 that includes a printed circuit board 1202 in accordance with embodiments of the present disclosure. Microfluidic chip 1101 is shown in FIG. 12, but it is understood that microfluidic chip 1100 can also be used without deviating from the scope of the disclosure. A printed circuit board 1202 is shown to be disposed on top of the microfluidic chip 1101. The term "on top of" here means that the fluid inlet 1112 and fluid outlet 1120 on a bottom side of the microfluidic chip 1101 are still exposed, and the printed circuit board 1202 is disposed on an opposite side of the microfluidic chip 1101 than the fluid inlet 1112 and fluid outlet 1120. Though referred to as a printed circuit board 1202, it is understood that a different type of structure or material can be used to act as an electrical and mechanical interface between the sensor elements and the underlying microfluidic chip 1101. The printed circuit board 1202 can be generalized to include a rigid structure, which can be used to provide electrical connectivity between the sensor 100 and outside electronics, as well as to provide structural stability for securing the sensor die 250 to the microfluidic chip sensor receiving portion 400. The rigid structure can be a printed circuit board (PCB), a metal surface, a polymer surface, etc.

The PCB 1202 can be secured to the microfluidic chip 1101 by a PCB alignment hole 1204. The PCB alignment hole 1204 can be a hole that lines up with PCB alignment structure 1122. As mentioned previously, the PCB alignment structure 1122 can be a protrusion that passes through the PCB alignment hole 1204. The PCB 1202 can be secured to the microfluidic chip 1101 by an adhesive 1302 (shown in FIG. 13B). An example adhesive is a UV-cured acrylated urethane, though other adhesives can be used.

The PCB 1202 can include a plurality of bonding pads 1208. Bonding pads 1208 can provide electrical connectivity to sensor back-side contacts, such as contacts 114 on sensor die 250. The bonding pads 1208 can be electrically coupled to a connector 1210 through embedded traces 1214. Embedded traces 1214 can be on a top-side, intermediate layer, or a bottom-side of the PCB 1202. Bonding pads 1208 can include vias 1206 to traces on the bottom-side or intermediate layer of the PCB 1202 to electrically connect some of the bonding pads 1208 with the connector 1210. The connector 1210 can include a plurality of gold fingers, each of which can be electrically isolated. Each gold finger can be used to send and receive electrical signals to and from a sensor. A reference electrode bonding pad 1212 can also reside on the PCB 1202 to bond to the reference electrode.

Figure 13A:
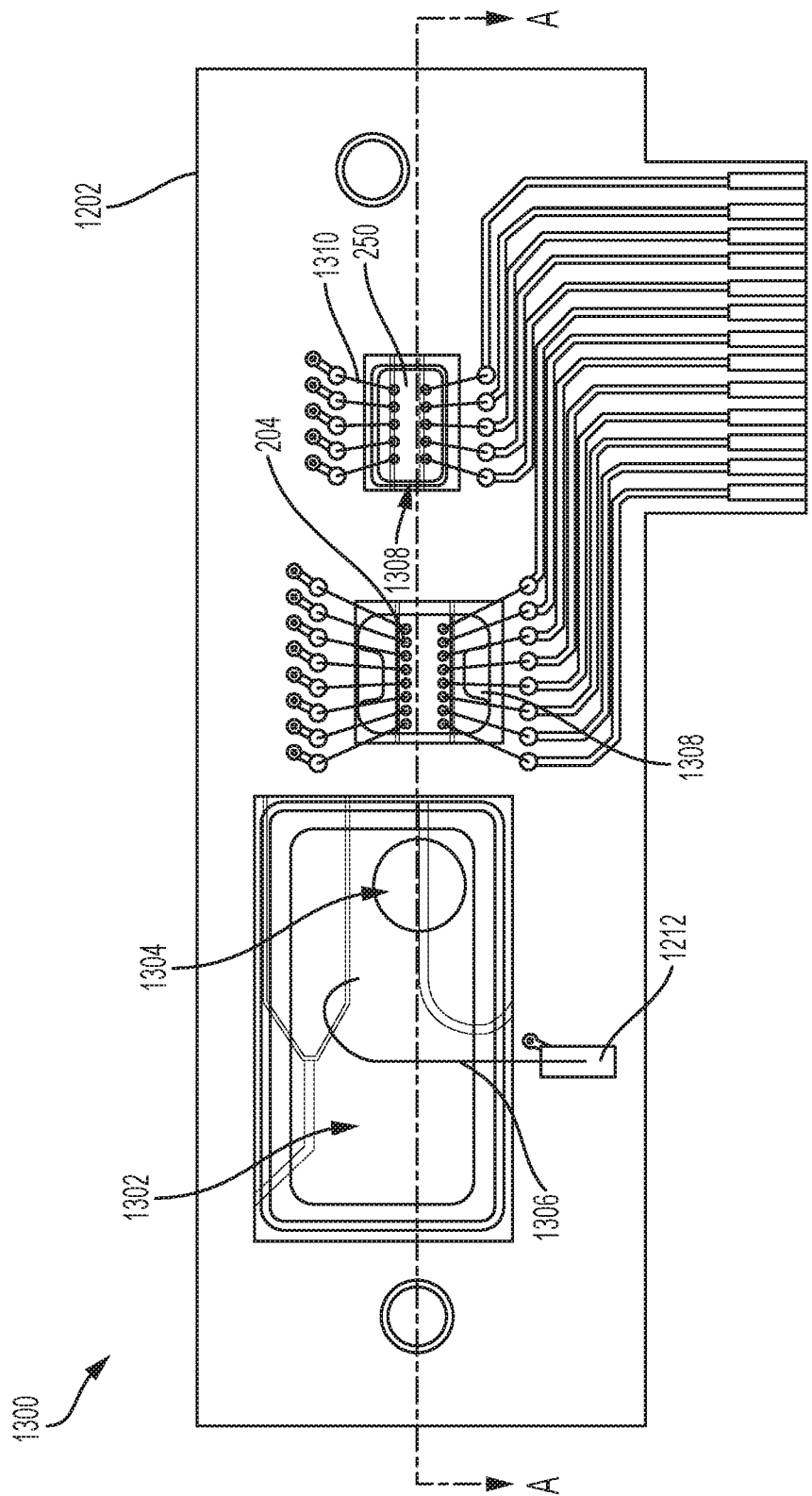
FIG. 13A is a top-down view of a schematic diagram of an assembled microfluidic chip in accordance with embodiments of the present disclosure.

FIG. 13A is a top-down view of a schematic diagram of an assembled microfluidic chip 1300 in accordance with embodiments of the present disclosure. The assembled microfluidic chip 1300 includes a reference electrode capsule 1302 and one or more chemical sensor dies 250. The sensor dies 250 are discussed further in FIG. 13B-FIG. 16. The reference electrode capsule 1302 can include a reference solution for making reference measurements. The reference electrode capsule can also include a ceramic frit 1304 that can act as a membrane. The ceramic frit 1304 can be of a porous material. The ceramic frit 1304 provides an ohmic path through the electrolyte solution that is contained in the reference electrode capsule 1302 and to the silver/silver chloride electrode. An electrode 1306 can electrically couple the reference electrode 1302 with the PCB 1202. The electrode 1306 can be silver (Ag) or silver chloride (AgCl). The electrode 1306 can be electrically coupled to the reference electrode bonding pad 1212.

The sensor die 250 can be secured to the microfluidic chip 1101 by an adhesive 1308. An example adhesive 1308 is a UV-cured acrylated urethane, though other adhesives can be used. The contact pads on the sensor die 250 can be electrically coupled to the printed circuit board 1202 by wire bonds 1310.

Figure 13B:
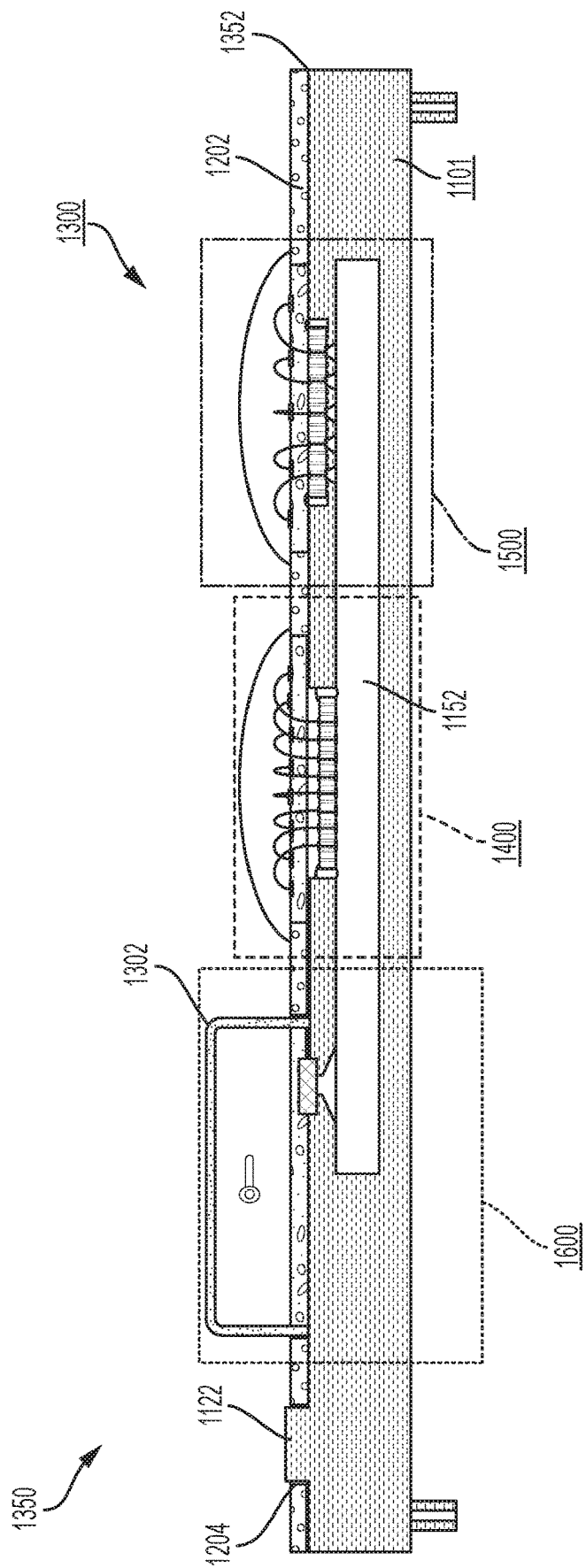
FIG. 13B is a side, cut away view of a schematic diagram of an assembled microfluidic chip in accordance with embodiments of the present disclosure.

FIG. 13B is a side, cut away view 1350 of a schematic diagram of an assembled microfluidic chip 1300 in accordance with embodiments of the present disclosure. The cut away view 1350 shows the PCB alignment structure 1122 within the PCB alignment hole 1204. The cut away 1350 also shows the fluid channel 1152. The PCB 1202 is secured to the microfluidic chip 1101 by an adhesive 1352.

Figure 15:
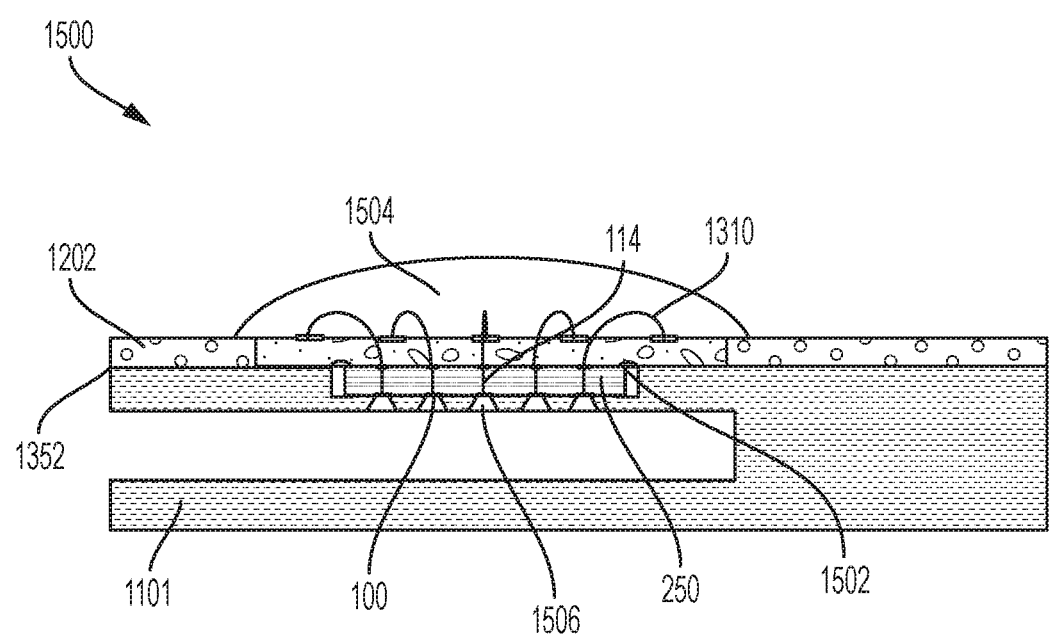
FIG. 15 is a close-up view of the side, cut away view of the assembled microfluidic chip showing a sensor die with clamped membranes in accordance with embodiments of the present disclosure.
Figure 16:
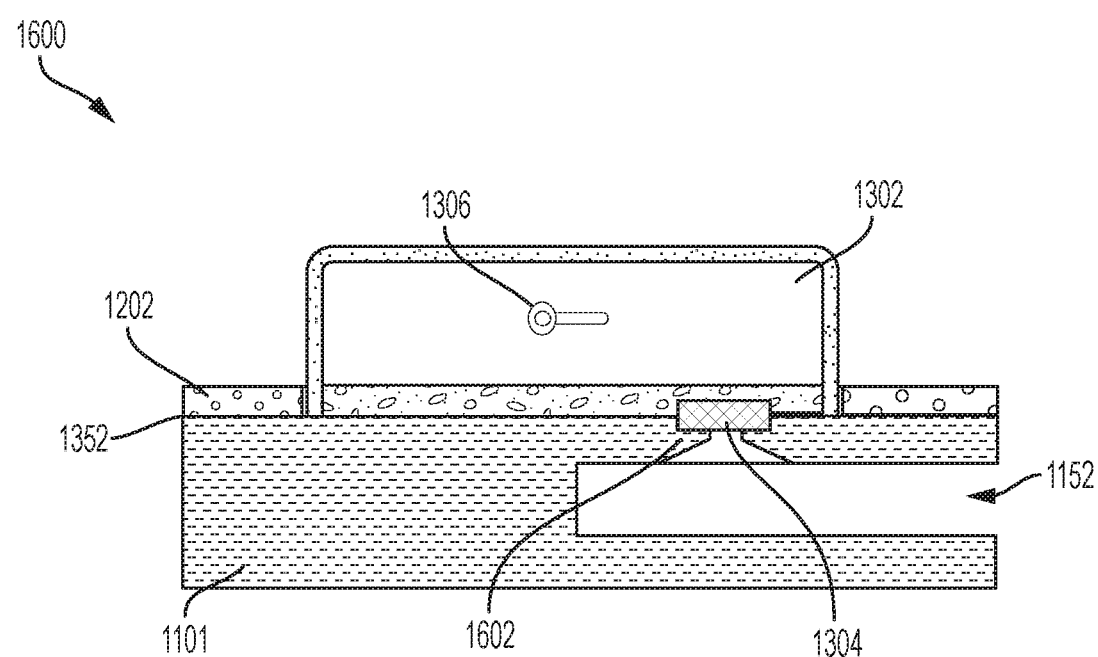
FIG. 16 is a close-up view of the side, cut away view of the assembled microfluidic chip showing a reference electrode in accordance with embodiments of the present disclosure.

The cut away view 1350 illustrates three areas of interest that are described in FIGS. 14-16: the amperometric sensor area 1400, the potentiometric sensor area 1500, and the reference electrode area 1600.

FIG. 14 is a close-up view of the side, cut away view of the assembled microfluidic chip showing an amperometric sensor area 1400 a fully exposed sensor area in accordance with embodiments of the present disclosure. As mentioned previously, the PCB 1202 is secured to the microfluidic chip 1101 by an adhesive 1352. A sensor die 250 is secured to the microfluidic chip 1101 by an adhesive 1402. The sensor die 250 includes a plurality of chemical sensors 100. The chemical sensors 100 are electrically connected by backside contacts 114 to the PCB 1202 by wire bonds 1310. The wire bonds and exposed electrical contacts can be protected and insulated by an encapsulant 1404.

The sensors 100 (and the entire sensor-side surface of the sensor die 250) are each fully exposed to the microfluidic channel 1152.

FIG. 15 is a close-up view of the side, cut away view of the assembled microfluidic chip showing a potentiometric sensor area 1500 with clamped membranes in accordance with embodiments of the present disclosure. The microfluidic chip 1101 is shown to include clamping structures 1506. Clamping structures 1506 can be similar to those discussed above in FIGS. 5-10B. The clamping structures 1506 can help secure the sensors 100 and the silicon die 250 to the microfluidic chip 1101. The clamping structures 1506 can also be structured to direct fluid towards to the sensors.

As mentioned previously, the PCB 1202 is secured to the microfluidic chip 1101 by an adhesive 1352. A sensor die 250 is secured to the microfluidic chip 1101 by an adhesive 1502. The sensor die 250 includes a plurality of chemical sensors 100. The chemical sensors 100 are electrically connected by backside contacts 114 to the PCB 1202 by wire bonds 1310. The wire bonds and exposed electrical contacts can be protected and insulated by an encapsulant 1504.

FIG. 16 is a close-up view of the side, cut away view of the assembled microfluidic chip showing a reference electrode in accordance with embodiments of the present disclosure. The reference electrode capsule 1302 is shown to include a reference fluid. The fluid can be coupled to an electrode 1306 that is wire bonded to an electrode on the PCB 1202. The reference electrode 1600 includes a ceramic frit or wick that is exposed to the microfluidic channel 1152 as well as the reference fluid within the capsule 1302. The ceramic frit 1304 can be secured using an adhesive 1602. As mentioned previously, the PCB 1202 is secured to the microfluidic chip 1101 by an adhesive 1352.

Aspects described in this disclosure can employ thin-film fabrication techniques to create the sensor devices and structures described herein, and to achieve advantages that are described herein and that are readily apparent to those of skill in the art.

Advantages of the present disclosure are readily apparent. Advantages of using the through-silicon via to connect to the micro ion-selective electrode facilitate a planar sensor surface on the sensor die. A planar sensor surface allows for the sensor die to be mounted over a microfluidic channel and for electrical contacts to be kept separated from the microfluidic channel. Electrical signals are available on the back side of the sensor die for convenient wire-bonding to pads on the printed circuit board. Bonding wires on the back side of the sensor die need not be insulated from the solutions that come into contact with the sensors, because they are separated from these solutions by the sensor die, itself.

While certain embodiments have been described in detail, those familiar with the art to which this disclosure relates will recognize various additional and/or alternative designs, embodiments, and process steps for making and using the sensor device as described by the following claims.

What is claimed is:

1. A system comprising:
a microfluidic chip;
a sensor device residing on the microfluidic chip, the sensor device comprising a silicon substrate comprising a sensor-side and a backside, the sensor-side comprising a chemical sensor and the backside comprising a backside electrode, the chemical sensor electrically coupled to the backside electrode by a through-silicon via, the through-silicon via physically and electrically connected to the chemical sensor, the through-silicon via extending from the chemical sensor through the silicon substrate towards the backside, the through-via electrically connecting the chemical sensor to the backside electrode;
a microfluidics channel in the microfluidic chip, the sensor-side of the sensor device facing the microfluidics channel;
a printed circuit board residing on the microfluidic chip, the printed circuit board comprising a top side and a bottom side, the bottom side contacting the microfluidic chip, the top side comprising an electrical contact; and
the electrical contact electrically connected to the backside electrode.

2. The system of claim 1, wherein the sensor device comprises one of an ion-selective sensor, an amperometric sensor, a thermal sensor, a conductivity sensor, a temperature sensor, or an oxidation reduction potential (ORP) sensor.

3. The system of claim 1, further comprising an encapsulant covering the sensor device backside and the electrical contact.

4. The system of claim 1, wherein the microfluidic chip comprises a fluid inlet and a fluid outlet downstream of the fluid inlet, the system further comprising a reference electrode downstream from the sensor device.

5. The system of claim 1, comprising a sensor die, the sensor device comprising a plurality of sensor devices.

6. The system of claim 1, wherein the microfluidic chip comprises a cutout portion, the cutout portion comprising a ledge, and wherein the sensor device is rigidly affixed to the ledge of the cutout portion.

7. The system of claim 1, further comprising a wire electrically connected to the electrical contact and electrically connecting the electrical contact to the backside electrode.

8. The system of claim 1, wherein the electrical contact comprises a POGO pin electrical interface.

9. The system of claim 1, wherein the electrical contact comprises one of gold bumps, pressure contacts, or wire bonds.

10. The system of claim 1, wherein the microfluidic chip comprises a fluid inlet and a fluid outlet downstream of the fluid inlet, wherein the sensor device is a first sensor device, and the microfluidic chip further comprises a second sensor device downstream of the first sensor device.

11. The system of claim 10, wherein the first sensor device comprises one of a potentiometric sensor or an amperometric sensor and the second sensor device comprises one of an amperometric sensor or a potentiometric sensor, respectively.

12. The system of claim 1, wherein the microfluidic chip comprises a clamping structure, the clamping structure comprising at least one raised portion to engage with a membrane of the sensor device to secure the sensor device to the microfluidic chip.

13. The system of claim 1, wherein the microfluidics channel comprises a serpentine shaped channel disposed below the sensor device.

14. A method for forming a microfluidic system comprising a sensor device, the method comprising:
providing a microfluidic chip, the microfluidic chip comprising a sensor device mounting surface, the sensor device mounting surface comprising a negative space revealing a microfluidic channel and a ledge residing over the microfluidic channel;
providing an adhesive on the ledge;
providing a sensor device on the ledge and securing the sensor device on the ledge by the adhesive, the sensor device comprising a sensor side and a backside, the sensor device positioned on the ledge with the sensor side facing the microfluidic channel;
providing a printed circuit board onto the microfluidic chip, the printed circuit board comprising an electrical contact pad;
electrically connecting a backside electrode on the sensor device to the electrical contact pad with a wire bond; and
providing an encapsulant on the sensor device, the electrical contact pad, and the wire bond.

15. The method of claim 14, wherein the backside electrode is electrically coupled to a sensor on the sensor side of the sensor device.

16. The method of claim 14, wherein the sensor side comprises one of a chemical sensor, an amperometric sensor, a thermal sensor, a conductivity sensor, a temperature sensor, or an oxidation reduction potential (ORP) sensor.

* * * * *

UNITED STATES PATENT AND TRADEMARK OFFICE
CERTIFICATE OF CORRECTION

| | |
|---|---|
| PATENT NO. | : 10,710,068 B2 |
| APPLICATION NO. | : 15/710823 |
| DATED | : July 14, 2020 |
| INVENTOR(S) | : Richard B. Brown and Ondrej Novak |

It is certified that error appears in the above-identified patent and that said Letters Patent is hereby corrected as shown below:

On the Title Page

Item (73) Assignee:, delete "e-SENSE, Inc." and insert -- e-SENS, Inc. --, therefor.

Signed and Sealed this
Eighteenth Day of July, 2023

Katherine Kelly Vidal
*Director of the United States Patent and Trademark Office*